(12) United States Patent
Lu et al.

(10) Patent No.: US 10,492,703 B2
(45) Date of Patent: Dec. 3, 2019

(54) EPIDERMAL SENSOR SYSTEM AND PROCESS

(71) Applicant: Board of Regents, The University of Texas System, Austin, TX (US)

(72) Inventors: Nanshu Lu, Austin, TX (US); Shixuan Yang, Austin, TX (US); Pulin Wang, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 627 days.

(21) Appl. No.: 14/671,554

(22) Filed: Mar. 27, 2015

(65) Prior Publication Data

US 2016/0278651 A1 Sep. 29, 2016
US 2017/0150896 A9 Jun. 1, 2017

Related U.S. Application Data

(60) Provisional application No. 61/971,945, filed on Mar. 28, 2014.

(51) Int. Cl.
*A61B 5/04* (2006.01)
*A61B 5/0408* (2006.01)
(Continued)

(52) U.S. Cl.
CPC ............. *A61B 5/0408* (2013.01); *A61B 5/01* (2013.01); *A61B 5/0492* (2013.01);
(Continued)

(58) Field of Classification Search
CPC .................................................. A61B 5/0408
See application file for complete search history.

(56) References Cited

U.S. PATENT DOCUMENTS

| 5,087,494 A | 2/1992 | Calhoun et al. |
| 5,494,730 A | 2/1996 | Calhoun |

(Continued)

FOREIGN PATENT DOCUMENTS

WO WO 2015/148957 10/2015

OTHER PUBLICATIONS

Schuettler, M. et al., "Fabrication of Implantable Microelectrode arrays by Laser Cutting of Silicone Rubber and Platinum Foil"—Journal of Neural Engineering, Institute of Physics Publishing, Bristol, GB, vol. 2, No. I, dated Mar. 1, 2005, pp. S121-S128 (8 pgs).*

(Continued)

*Primary Examiner* — Eric D. Bertram
(74) *Attorney, Agent, or Firm* — DLA Piper LLP (US)

(57) ABSTRACT

Epidermal electronics are sensors with mechanical properties matching human epidermis. Their manufacturing process includes photolithography and dry and wet etching within cleanroom facilities. The high cost of manpower, materials, photo masks, and facilities greatly hinders the commercialization potential of disposable epidermal electronics. In contrast, an embodiment of the invention includes a low cost, high throughput, bench top "cut-and-paste" method to complete the freeform manufacture of epidermal sensor system (ESS) in minutes. This versatile method works for many types of thin metal and polymeric sheets and is compatible with many tattoo adhesives or medical tapes. The resultant ESS is highly multimaterial and multifunctional and may measure ECG, EMG, skin temperature, skin hydration, as well as respiratory rate. Also, a stretchable planar coil made of serpentine ribbons can be used as a wireless strain gauge and/or a near field communication (NFC) antenna. Other embodiments are described herein.

13 Claims, 14 Drawing Sheets

(51) Int. Cl.

| | |
|---|---|
| *A61B 5/0492* | (2006.01) |
| *A61B 5/053* | (2006.01) |
| *A61B 5/01* | (2006.01) |
| *A61B 5/085* | (2006.01) |
| *A61B 5/00* | (2006.01) |
| *B29C 35/02* | (2006.01) |
| *B29K 67/00* | (2006.01) |
| *B29L 31/00* | (2006.01) |

(52) U.S. Cl.
CPC ............ *A61B 5/0537* (2013.01); *A61B 5/085* (2013.01); *A61B 5/6833* (2013.01); *B29C 35/02* (2013.01); *A61B 2562/125* (2013.01); *B29K 2067/003* (2013.01); *B29L 2031/753* (2013.01)

(56) References Cited

U.S. PATENT DOCUMENTS

| | | | |
|---|---|---|---|
| 8,097,926 B2 | 1/2012 | De Graff et al. | |
| 8,207,473 B2 | 6/2012 | Axisa et al. | |
| 8,886,334 B2 | 11/2014 | Ghaffari et al. | |
| 8,978,452 B2 | 3/2015 | Johnson et al. | |
| 9,119,533 B2 | 9/2015 | Ghaffari | |
| 2006/0183989 A1* | 8/2006 | Healy | A61B 5/04087 600/372 |
| 2009/0165569 A1* | 7/2009 | Taya | G01D 5/14 73/862.041 |
| 2011/0184269 A1 | 7/2011 | Fabien et al. | |
| 2011/0230747 A1 | 9/2011 | Rogers | |
| 2012/0157804 A1 | 6/2012 | Rogers | |
| 2012/0190989 A1 | 7/2012 | Kaiser | |
| 2013/0036802 A1* | 2/2013 | Johnson | G01N 27/223 73/74 |
| 2013/0041235 A1 | 2/2013 | Rogers | |
| 2013/0072775 A1 | 3/2013 | Rogers | |
| 2013/0333094 A1 | 3/2013 | Rogers | |
| 2013/0245388 A1* | 9/2013 | Rafferty | A61B 5/6831 600/301 |
| 2013/0255396 A1 | 10/2013 | Cho et al. | |
| 2016/0004952 A1 | 1/2016 | Mei | |

OTHER PUBLICATIONS

International Searching Authority, "Notification of Transmittal of the International Search Report and the Written Opinion of the International Searching Authority," dated Sep. 4, 2015 in International application No. PCT/US2015/023052.

Kim, Jeonghyun, et al., "Epidermal Electronics with Advanced Capabilities in Near-Field Communication," Communications, Stretchable Electronics, Small, 2015, 11, No. 8, pp. 906-912, 8 Pages.

Kim, Dae-Hyeong et al., "Epidermal Electronics," Science Mag, vol. 333, Aug. 2011, 46 Pages.

Ying, Ming et al., "Silicon nanomembranes for fingertip electronics," Nanotechnology, vol. 23, No. 34, Aug. 2012, 20 Pages.

Silhouette America Website, "http://www.silhouetteamerica.com/shop/machines/cameo," accessed Mar. 5, 2015, 4 Pages.

3M Website "http://solutions.3m.com/wps/portal/3M/en_EU/Healthcare-Europe/," accessed Mar. 6, 2015, 1 Page.

Schuettler, M. et al., *"Fabrication of Implantable Microelectrode arrays by Laser Cutting of Silicone Rubber and Platinum Foil"*— Journal of Neural Engineering, Institute of Physics Publishing, Bristol, GB, vol. 2, No. 1, dated Mar. 1, 2005, pp. S121-S128 (8 pgs).

\* cited by examiner

900

- 905: Provide first conductive element (e.g., metal such as Au or Al or semiconductor element such as Si) on first substrate (e.g., polymer such as PET).
- 910: Bond first conductive element to second substrate (e.g., TRT) to form a composite and couple second substrate to manufacturing platform (e.g., cutting pad).
- 915: Position composite in forming tool (e.g., knife or laser based construction tool configured to form strands from first conductive element).
- 920: Form patterns (e.g., strands) in first conductive element.
- 925: Expose composite to heat
- 930: Remove unwanted first conductive element portions from composite.
- 935: Couple composite to third substrate (e.g., skin tape) and remove second substrate.
- 940: Couple composite to fourth substrate (e.g., liner to keep Au strands from premature exposure).
- 945: Position multiple ESS on continuous deployment system (e.g., large roll of ESS whereby perforations allow ESS to be removed from deployment system one by one).

FIG. 9

EPIDERMAL SENSOR SYSTEM AND PROCESS

PRIORITY CLAIM

This application claims priority to U.S. Provisional Patent Application Ser. No. 61/971,945, filed Mar. 28, 2014, the content of which is hereby incorporated by reference.

FUNDING

This invention was made with government support under Grant nos. CMMI1301335, and CMMI1351875 awarded by the National Science Foundation. The government has certain rights in the invention.

TECHNICAL FIELD

Embodiments of the invention are in the field of flexible and stretchable sensors.

BACKGROUND

An animal body radiates data about itself. Wearable devices that can transmit information from a body (e.g., animal or human) have the ability to transform two prominent fields: mobile health (mHealth) and human-machine interface (HMI). In addition to fitness tracking, long term tracking of physiological signals helps in the detection of heart failure, epilepsy, and other conditions. However, wafer-based electronics remain intrinsically planar, rigid, and brittle. As a result, state-of-the-art integrated circuit (IC)-based wearable devices are in the form factors of "chips on tapes" or "bricks on straps", which are unable to maintain intimate and prolonged contact with a curved, soft, and dynamic human body to retrieve long-term, high-fidelity physiological signals.

Recent advancements in flexible and stretchable electronics have provided viable solutions to the intimate integration of electronics with bio-systems. Among many breakthroughs, an epidermal electronic system(s) represents a wearable device whose mechanical properties match that of human skin. As a result, an epidermal electronic system can conform to human skin like a temporary transfer tattoo and deform like a natural extension of the skin without detachment or fracture. An epidermal electronic system may monitor electrophysiological signals, skin temperature, skin hydration, sweat, and motion disorders.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 9 includes a process for forming an epidermal sensor system (ESS) in an embodiment of the invention.

DETAILED DESCRIPTION

Figure 1A:
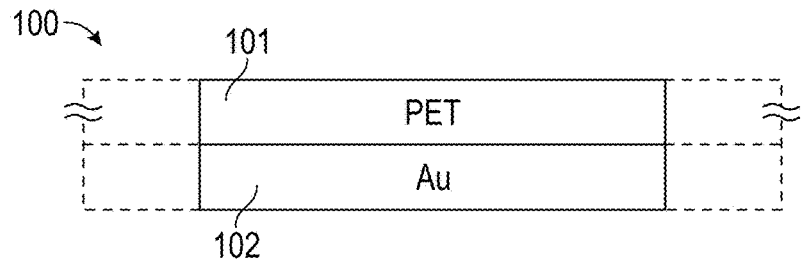
FIGS. 1(a)-(h) depict a process in an embodiment of the invention.

Reference will now be made to the drawings wherein like structures may be provided with like suffix reference designations. In order to show the structures of various embodiments more clearly, the drawings included herein are diagrammatic representations of sensor/circuit structures. Thus, the actual appearance of the fabricated integrated circuit structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. For example, not every layer of a semiconductor device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

The thinness and softness of conventional epidermal electronic systems leads to collapsing and crumpling of the devices after they are peeled off human skin, making their ideal use temporary. As a result, the success of epidermal electronic system technology hinges on the realization of low cost, high throughput manufacture of the devices. However, current manufacture of epidermal electronic systems relies on standard microfabrication processes including spin coating, photolithography, wet or dry etching, and transfer-printing. Although it has been proven effective, there are several limitations associated with such a process. First, the high cost associated with cleanroom facilities, photo masks, and photolithography chemicals prevents epidermal sensors from being low cost enough to be disposable. Second, the high vacuum processes can be very time consuming and impractical for thick metal deposition. Third, the epidermal electronic system size is limited to the wafer size which has to compatible with all the vacuum chambers. Fourth, the manpower-demanding manufacturing process greatly limits the accessibility of epidermal electronic systems to academic research.

In contrast, an embodiment provides a "cut-and-paste" method for creating an "epidermal sensor system" (ESS)

that offers a very simple solution to the abovementioned challenges. Instead of performing high vacuum metal deposition, thin metal-on-polymer laminates of various thicknesses can be directly purchased from industrial manufacturers of shielding tapes. Instead of using photolithography patterning, a bench top electronic cutting machine is used to mechanically carve out the designed ribbon shapes (or other shapes) with excess material being removed. This is a free-form manufacturing process that is the inverse to popular additive manufacturing technologies. Since the patterns can be formed directly on thermal release tapes (TRT), the patterned ribbons can be directly printed onto a variety of types of tattoo adhesives and medical tapes without a "picking up" step (e.g., such as when a polydimethylsiloxane (PDMS) stamp is used to transfer silicon epidermal electronic system components from a substrate). In an embodiment, some cutting machines form patterns on thin sheet metals and polymers up to 12 inches wide and several feet long (while other such machines may handle wider or longer materials), which exceeds lab-scale wafer size (thereby increasing through put and lowering costs as compared to lithography based processes). The whole process can be completed on a bench top in minutes (e.g., 10 minutes) without using a wet process (e.g., wet etching), which affords very fast training of the technicians that make the product and an overall easy turnaround.

As shown in embodiments described herein, multimaterial ESS are fabricated using the "cut-and-paste" technology. The resultant ESS has been successfully applied to measure electrocardiogram (ECG), electromyogram (EMG), electroencephalogram (EEG), skin temperature, skin hydration, and respiratory rate. In an embodiment, planar stretchable coils of thick aluminum ribbons are also integrated on the ESS as a wireless strain gauge. The strain gauge also serves as an antenna (e.g., NFC antenna) in some embodiments.

FIGS. 1(a)-(h) depict a process in an embodiment of the invention, including a schematic of the bench top "cut-and-paste" process. Since polymer-supported metal thin films are much more stretchable than freestanding metal sheets, an embodiment uses polymer-supported metal sheets as the starting materials. Starting materials, including gold coated polyimide or aluminum laminated polyethylene terephthalate (PET), can be purchased from industrial vendors. An embodiment uses thermal evaporation to deposit 100 nm gold film 102 on 13 μm transparent PET tape 101 (FIG. 1(a), Element 905 of FIG. 9).

Figure 1B:
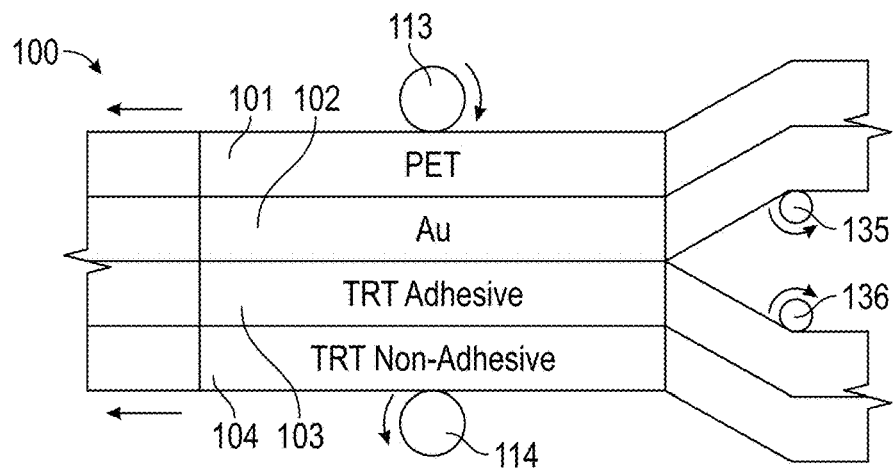

To manufacture gold-based stretchable electrophysiological (EP) electrodes, temperature sensors, and concentric dot-ring impedance sensors, the gold coated PET sheet is uniformly bonded to a thermal release tape with the gold side facing the TRT adhesive side 103, as shown in FIG. 1(b) (see also element 910 of FIG. 9). The other side of the TRT 104 is adhered or placed on a cutting mat, as shown in FIG. 1(c) (see also element 910 of FIG. 9).

As seen in FIGS. 1(b)(e)(f), PET layer 101, Au layer 102, TRT adhesive layer 103, and TRT layer 104 are all parts of long lengths of material fed (right to left or vice versa) by rollers 113, 114, 131, 132, 133, 134 or other conveyor tools known in the manufacturing arts. This is not possible with stiff silicon wafers, photolithography tools, clean rooms, and the like.

Figure 1C:
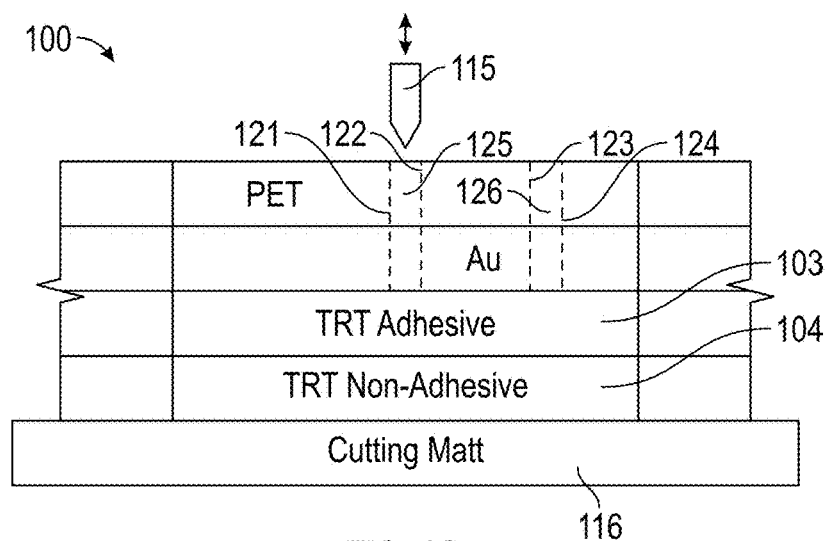

In FIG. 1(c) the cutting mat 116 is fed into an electronic cutting machine (e.g., Silhouette CAMEO®, Silhouette America, Inc., West Orem, Utah, USA) with the PET side 101 facing up towards cutting tool 115 (element 915 of FIG. 9). While the cutting tool may be a knife or sharp object in some embodiments, it may be a laser or other cutting tool in other embodiments. By importing designs generated by commercial software (e.g., AutoCAD® design) into the cutting machine, the cutting machine automatically carves the Au/PET sheets 101, 102 with customized patterned cuts 121, 122, 123, 124 to yield desired patterns 125, 126 (FIG. 1(c) and element 920 of FIG. 9). Cutting machines are fully capable of generating features with 200 μm resolution (although other embodiments may have finer or greater resolution) with acceptable feature uniformity and roughness.

Figure 1D:
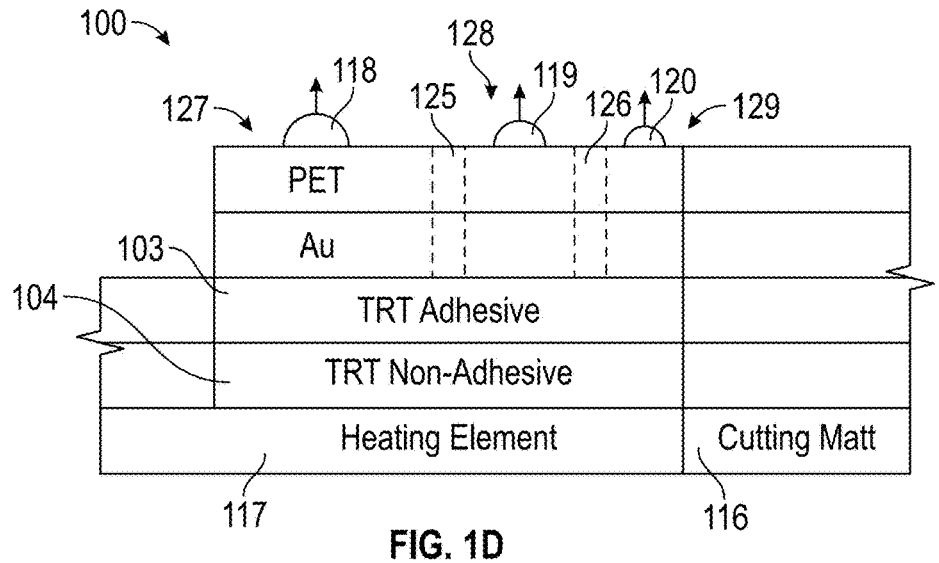

Once patterns 125, 126 are formed, the TRT is removed from the cutting mat (FIG. 1(d)) over heating element 117 at 115° C. for 1~2 minutes (see element 925 of FIG. 9). In other embodiments the heating element may be coupled to the cutting tool so the composite does not need to be removed from the cutting tool in order to deactivate the adhesive components of the TRT. Exposure to the heating element deactivates the adhesive 103 on the TRT tape so that the excessive portions 127, 128, 129 can be removed from the TRT (FIG. 1(d) and element 930 of FIG. 9), leaving only the device patterns 125, 126 loosely resting on the TRT (FIG. 1(e)). They may be removed by manually peeling off portions 127, 128, 129. In other embodiments they may be removed using vacuum/pressure gradient cups 118, 119, 120. In other embodiments they may be removed using patterned adhesives that align with material to be removed.

Figure 1E:
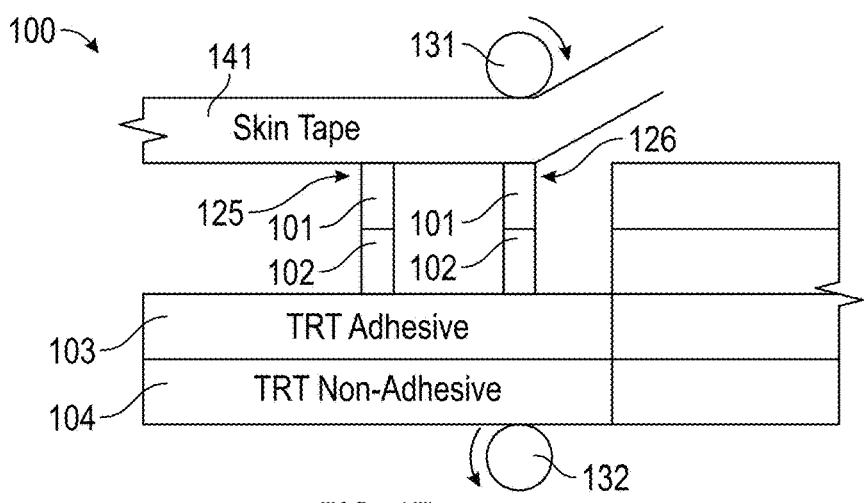
Figure 1F:
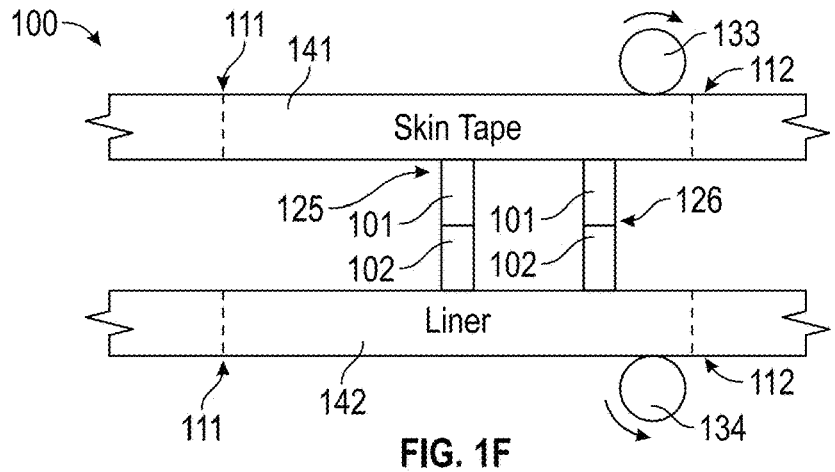

The device patterns will be printed onto a target substrate with native adhesives, such as skin tape 141 or a tattoo adhesive (e.g., Silhouette® temporary tattoo paper), medical tape transparent dressing (e.g., 3M Tegaderm™), or 3M® type removal silicone tape (FIG. 1(e) and element 935 of FIG. 9), yielding a gold-based ESS (FIG. 1(f) that is covered with liner 142 until ready for use (see element 940 of FIG. 9).

Figure 1G:
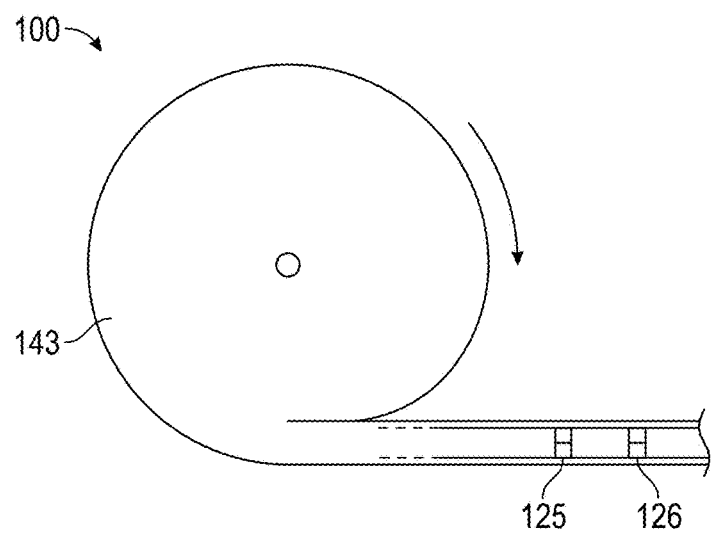
Figure 1H:
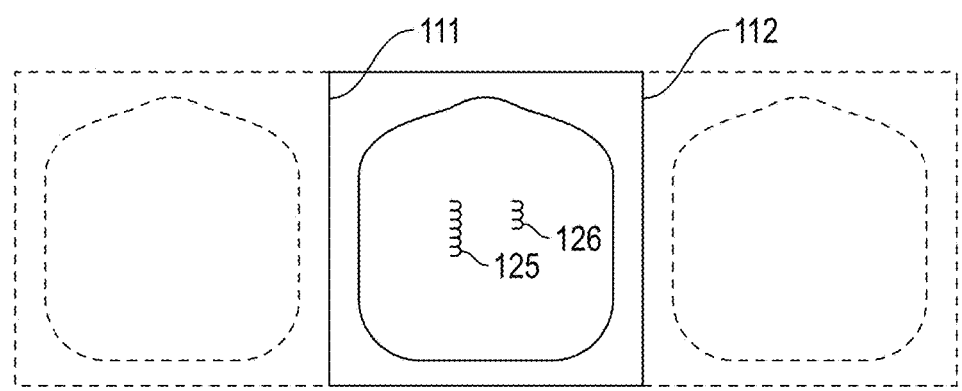

Once printed and lined, the ESS (along with other ESS printed before and after the ESS focused upon in FIGS. 1(a)-(f)) are stored in a roll 143 (FIG. 1(g)). In other words, the process in FIGS. 1(a)-(f) is repeated in assembly line fashion creating a long strip of disposable ESS that are easily stored, transported, and deployed from roll 143, or a folded sheet, and the like. Individual ESS can then be removed at perforations 111, 112 (see FIG. 1(h) and element 945 of FIG. 9). FIG. 1(h) includes a portion from a roll or strip of ESSs including perforated portions 111, 112 around an ESS including sensors 125, 126. Additional ESS are located on either side of the ESS including sensors 125, 126.

In an embodiment the process in FIGS. 1(a)-(f) is repeated but with other thin sheets of metals and polymers (e.g., using Al instead of Au 102 to form patterns that are formed on skin tape 141 and liner 142, such as an antenna coil or strain gauge) rendering a multimaterial, multiparametric ESS all on a final tape. In other words, the process may be repeated to form layers of ESS systems upon one another or the ESS may be interspersed with each other (addressed in regard to FIG. 8).

Design and Skin Integration of Multiparametric ESS

Figure 2A:
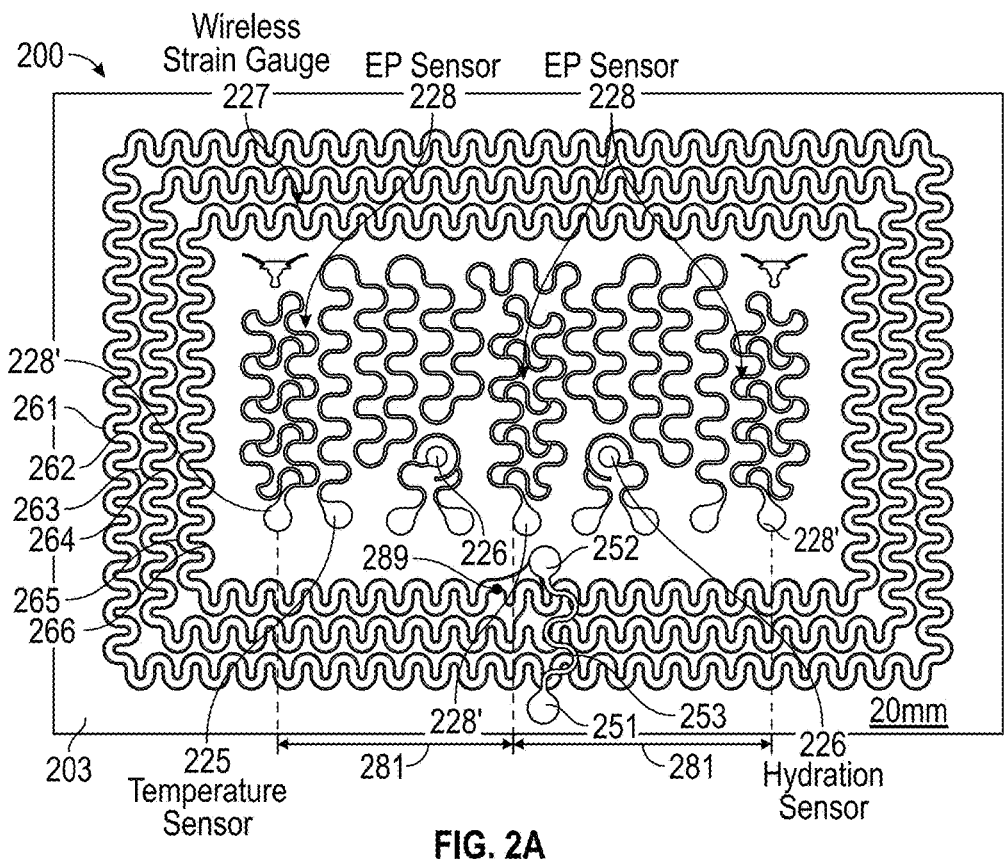
FIGS. 2(a)-(b) depict a sensor in an embodiment of the invention.
Figure 2B:
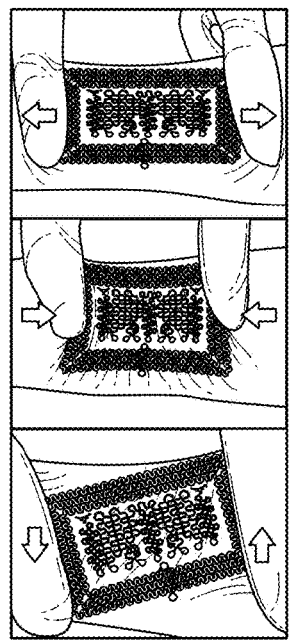
Figure 3A:
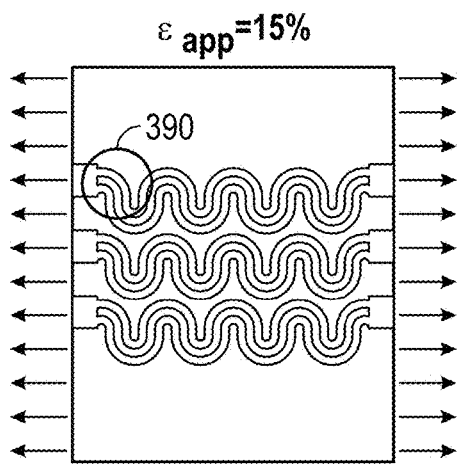
FIGS. 3(a)-(f) address strain in various embodiments of the invention.
Figure 3B:
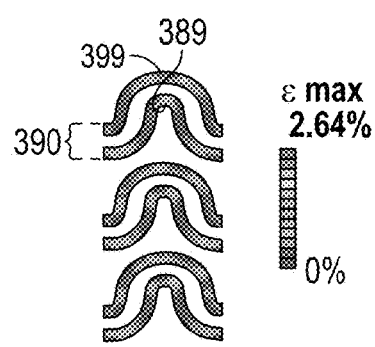
Figure 3C:
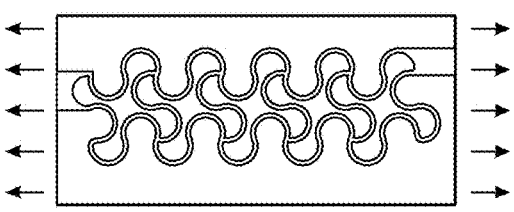
Figure 3D:
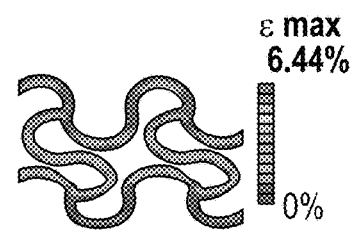
Figure 3E:
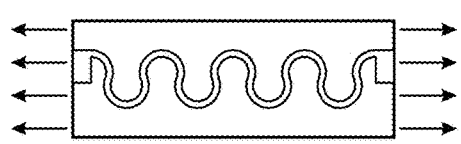
Figure 3F:
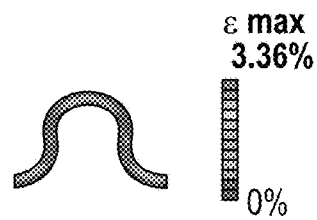
Figure 4A:
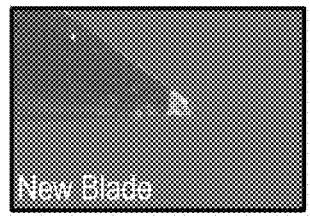
FIGS. 4(a)-(l) include images of various embodiments of the invention.
Figure 4B:
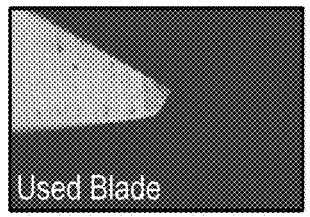
Figure 4C:
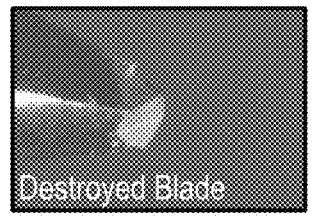
Figure 4D:
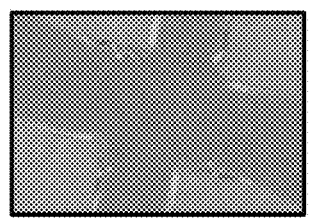
Figure 4E:
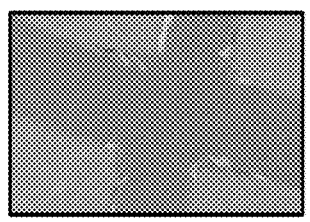
Figure 4F:
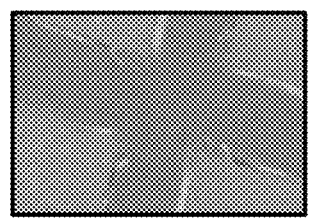
Figure 4G:
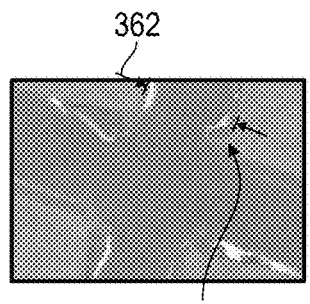
Figure 4H:
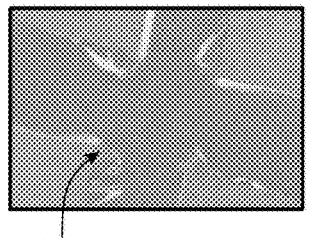
Figure 4I:
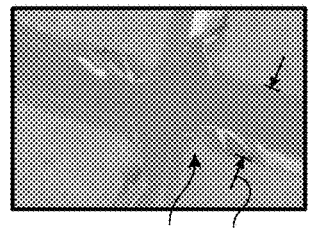
Figure 4J:
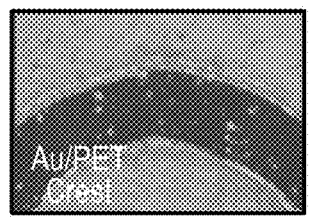
Figure 4K:
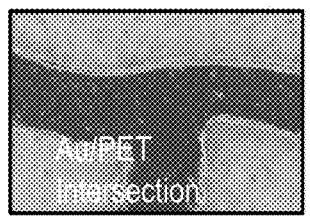
Figure 4L:
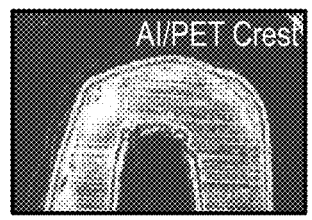

FIGS. 2(a)-(b) depict a sensor in an embodiment of the invention, including a multimaterial, multiparametric ESS printed on tattoo paper (Silhouette). In FIG. 2(a) ESS 200 includes three filamentary serpentine (FS) gold EP electrodes 228, one FS gold resistance temperature detector (RTD) 225, two dot-ring gold impedance sensors (226) that function as hydration sensors. ESS 200 also includes a planar FS coil (227) based on Al ribbons with Al facing skin tape 203, which functions as a wireless strain gauge and also as a NFC antenna. ESS 200 is stretchable as seen in the three pictures of FIG. 2(b). For the three FS EP electrodes 228, the inter-electrode distance 281 is set to be 2 cm for effective EP signal recording. The FS electrodes 228 are designed with ⅕ ribbon width to arc radius to balance the trade-off between stretchability and real estate. The same design is not applicable to the Al coil 227 because the coil would consume too much space for an ESS.

In an embodiment, coil 227 is designed by taking into account inductance, stretchability, and overall size. The resonant frequency (f) of a RLC circuit depends on its inductance and capacitance determined through the equation:

$$f = \frac{1}{2\pi\sqrt{LC}} \quad (1)$$

in which L is the inductance and C is the capacitance. An embodiment includes a low frequency coil that operates <100 MHz for purposes of easier measurement. In some embodiments, the same low frequency coil is used as an NFC coil. Equation (1) suggests the coil should have high inductance and/or capacitance to have a lower resonant frequency in an embodiment.

The capacitance of a parallel-plate capacitor is given by:

$$C = \varepsilon \frac{A}{d} \quad (2)$$

where ε denotes the absolute permittivity of the dielectric layer, A is the overlapped area of the parallel plates, and d is the thickness of the dielectric layer between the plates. There is an upper limit of the feasible capacitance for an ESS since the area of the parallel plate cannot be too large for a skin based system, the dielectric thickness cannot be too small, and some embodiments do not include rigid chip capacitors.

Therefore, in lieu of a large capacitance, a coil with large inductance is used in some embodiments. Another reason it is desirable to have the resonant frequency largely set by the inductor (in some embodiments) is that any change in strain produces a large change in the inductance. Thus, the frequency shift is more sensitive to strain. Inductance depends on the layout of the circuit. For a planar circuit inductance depends on the number of turns, shape of the turns, and the area that is covered by the circuit. In general, the larger the area and the more turns—the higher the inductance. However, this conflicts with the need of building a wireless strain gauge that is reasonably small so that it can be properly fitted on the majority of parts of the body. An embodiment also has a coil that is highly stretchable and compliant so that the coil does not mechanically load the skin.

With the aforementioned coil characteristics and/or challenges in mind, an embodiment includes a double-stranded serpentine design 227 in FIG. 2(*a*). For example, strands 261, 262 compose one double strand, strands 263, 264 compose another double strand, and strands 265, 266 compose yet another double strand. This design helps maximize the use of limited real estate to fill in as many serpentine-shaped turns as possible. Meanwhile it leaves reasonable gaps between serpentine portions so stretchability of the coil is ensured (FIGS. 3(*a*) and (*b*), FIG. 5(*c*)). Embodiments include coil 227 along the outer periphery of the ESS patch with the coil surrounding sensors, such as ECG sensors.

Figure 8:
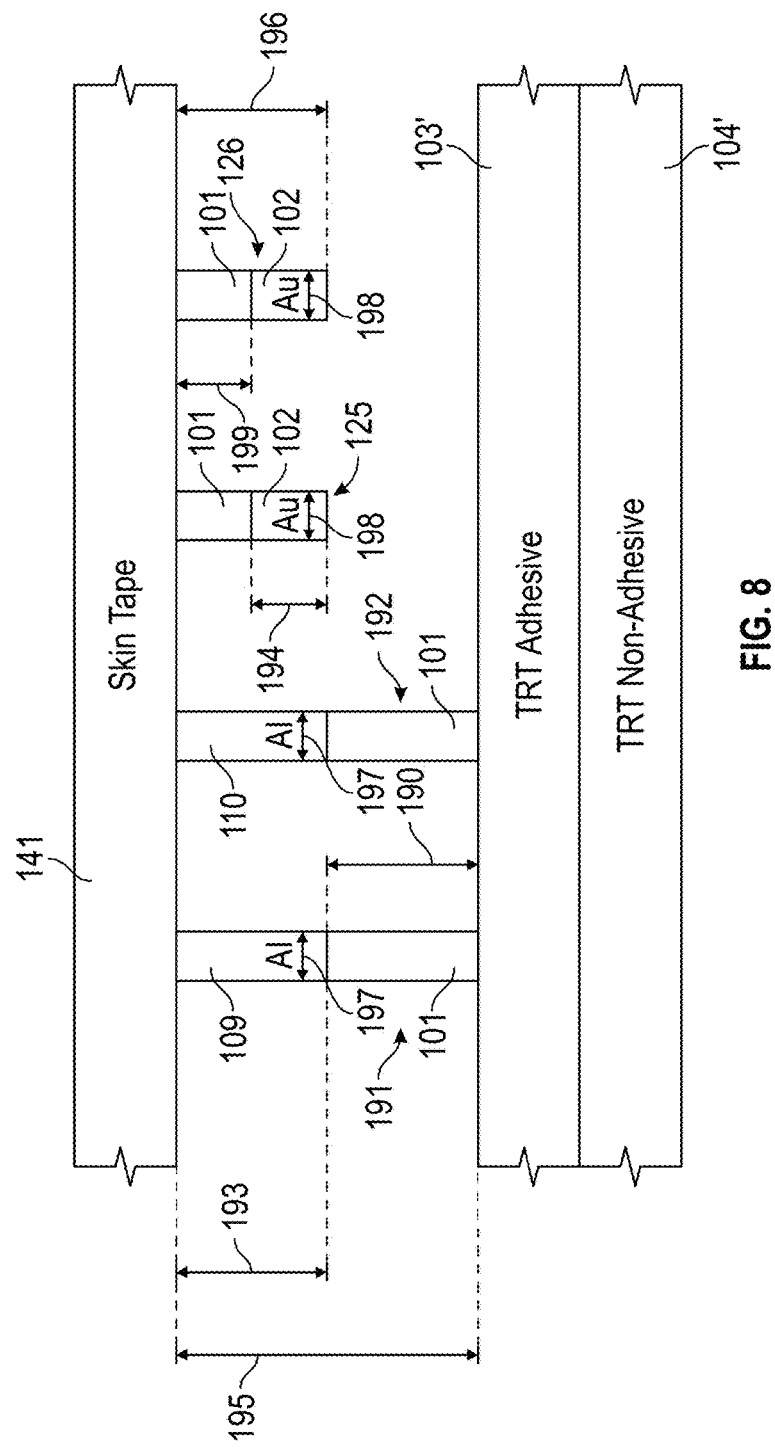
FIG. 8 depicts a process stage in an embodiment of the invention.

The two gold "long-horns" designs at the upper left and right corners of patch 200 serve as alignment markers for consecutive printings of different materials on the same tape (e.g., see FIG. 8 and related discussion). In an embodiment, the overall size of the device area is 7.5 cm×5 cm, which is supported by a 6"×8" large and 47 μm thick skin tape 203.

The Young's moduli of the different polymers used in ESS vary. Tegaderm™ is the most compliant of all polymers measured. Its modulus (7.4 MPa) is close to the high end of the modulus of human skin (0.32~4 MPa). The stretchability of different serpentine shapes and materials were tested and modeled. Electromechanical measurement with in situ top down observation was used to conduct the stretchability measurements. When electrical resistance is measured as a function of the applied uniaxial tensile strain, the applied strain at which the resistance increases dramatically/"explodes" is considered the strain-to-rupture or stretchability. While straight Al_PET and Au_PET ribbons exhibit very limited stretchability (2.89% and 13.72%, respectively), their serpentine counterparts are much more stretchable (all of which exceed the elastic limit of human skin (30%)). Al serpentine patterns 227 rupture at a strain of 68%, at which point failure points at the serpentine crests can be observed. The gold EP sensor 228 exploits a FS network design, which ruptures at a strain of 115%, with failure points at strand intersections. The gold RTD sensor 225 consists of one-dimensional (1D) FS serpentine ribbons, which demonstrates the largest stretchability (199%) among sensors 225, 227, 228, and fracturing sites are found again at the crest of the serpentine strands. The location of rupture can be predicted by finding the maximum principal strain using finite element modeling (FEM). FEM models (FIGS. 3(*b*), (*d*), (*f*)) were created for three different serpentine strands (FIGS. 3(*a*), (*c*), (*e*)). While the maximum strain occurs at the crests of 1D serpentines (FIGS. 3(*b*) and (*f*)), FS networks are most vulnerable at the intersections of orthogonal serpentine ribbons due to strain concentration (FIG. 3(*d*)).

The interaction of ESS on different skin tapes and human skin varies. While Tegaderm™ and tattoo papers are thin, transparent, and truly skin-like, a cloth tape (3M™ Kind Removal Silicone Tape) is much thicker. However, although Tegaderm™ and tattoo paper are one time use, the cloth tape does not crumple after being peeled off from the skin and the silicone adhesive allows multiple uses before losing adhesion. The electrical resistance of the Au and Al serpentines before and after various kinds of skin deformation (stretching, compression, shear, poking, etc.) is very consistent with little to no change between "before" stretching resistance and "after" stretching resistance. It is evident that the ESS can survive most possible skin deformations that the skin is able to experience.

Au-Based EP, Skin Temperature, and Skin Hydration Sensors

An embodiment including a multiparametric ESS has been successfully applied to perform real time, continuous measurements on EP, skin temperature, skin hydration, and respiratory rate. Embodiments of the Au and Al based sensors are shown in FIG. 2(*a*). EP signals on the surface of human skin pertain to the flow of ions in biological tissues and organs, and reflect the function and health of them. For example, EEG measured from the surface of a human brain not only captures cognitive and memory performance, but also reflects brain disorders like epilepsy and stroke. Non-invasive ambulatory monitoring of ECG on a human chest help detect an irregular heartbeat (e.g., arrhythmia). EMG measured on a human muscle helps identify neuromuscular diseases and can also serve as a control signal for prosthetic devices or other machines.

There are three FS EP sensors integrated on the ESS patch (collectively labeled 228). One acts as a reference to eliminate ground noise, and the differential between the other two sensors are the EP signals. The skin surface is first lightly abrased with a paper towel to remove dead skin, then wiped down with an alcohol swab to remove any skin oils. After the skin preparation, Applicants applied one ESS (see embodiment of FIG. 2(a)) and two conventional Ag/AgCl electrodes on the left chest. Simultaneously measured ECG waveforms (measured by connecting conventional Ag/AgCl gel electrodes and the ESS electrodes) were sent to an EP recorder, recorded, and processed using moving average calculations and DC offset compensation. The heart rate is generally identical from both measurements, with the ESS actually able to reveal more subtle features of ECG (e.g., better capability to sense weak signals on the chest) than the Ag/AgCl gel electrodes.

Muscle activity is reflected by EMG. Applicant placed the same ESS embodiment (FIG. 2(a)) over the forearm (specifically on the flexor muscles) to measure EMG. Two instance of hand clenching action were recorded via the ESS. The intensity of the gripping force was measured by a commercial dynamometer with a higher gripping force corresponding to a larger amplitude in the measured EMG. The ESS provided reliable and accurate measurements.

Applicant measured EEG by adhering conventional Ag/AgCl electrodes and the ESS (FIG. 2(a)) on a human forehead with a reference FS electrode behind the human ear. There was remarkable agreement between conventional and ESS measured EEG and their FFT spectrums almost fully overlap. Also, the spectrum of eye open and eye-closed EEG were both measured by ESS. The alpha rhythm (10 Hz peak) clearly shows up when an awakened subject closes his eyes.

In addition to EP, skin temperature and skin hydration are also useful indicators of human physiology. For example, skin temperature is associated with cardiovascular health, cognitive state, malignancy, and the like. Skin hydration is widely used in dermatology and cosmetology for the detection of diseases (e.g., eczema, atopic dermatitis, and the like), the assessment of mental stress or hormone levels, and the evaluation of medical therapies or cosmetic treatments.

Temperature fluctuation affects the collision of electrons in metals, resulting in a change in resistance. The Resistance Temperature Detector (RTD) 225 is made of wavy serpentine gold film (100 nm in thickness) in an embodiment, which are patterned in a confined area. Due to the serpentine shape the overall length of the RTD is around 0.3 m. Applicant performed a calibration test by placing both RTD 225 and a commercial thermal couple on a hotplate at the same time and recording the resistance of the RTD and reading of the thermal couple while the temperature of the hotplate was increased gradually. The results indicate the fractional change of the resistance is linearly proportional to temperature, which is $$\frac{\Delta R}{R} = \alpha(T - T_0) \quad (3)$$

in which $\alpha$ is the temperature coefficient of resistance, T is the increased temperature, and $T_o$ is the original temperature before the temperature is increased to T, R is the original resistance before the temperature is increased (i.e., R at $T_o$), and $\Delta R$ is the change in resistance brought on by change in temperature. The $\alpha$ for the RTD is $0.00169°$ $C^{-1}$, which is in good agreement with standard temperature coefficient of resistance for gold, which is $0.0034°$ $C^{-1}$. Next Applicant performed the temperature measurement on a human forearm by using epidermal RTD 225, along with the same thermal couple for reference. At the beginning the temperature of the skin is stabilized at 30 degree C. and at around $100^{th}$ second and $180^{th}$ second an ice bag is brought around the skin (where the sensors are mounted) and then taken away, respectively. The results indicate that epidermal RTD 225 successfully indicates (as well as the thermocouple) the change of the temperature (i.e., that the skin temperature drops when the ice bag is applied and skin temperature recovers when the ice bag is withdrawn). In addition, epidermal RTD 225 is much more compliant than the thermal couple, which has a polyimide encapsulated rigid sensor as the probing tip.

For skin hydration monitoring, the hydration sensor (H sensor) 226 is fabricated on the ESS by the aforementioned cut-and-paste process. Sensor 226 was operated by measuring hydration with a moisture meter (e.g., MoistureMeterSC Compact, Delfin Inc.), which is utilized for a calibration curve converting impedance to hydration level. Hydration sensor 225 in ESS patch 200 measured the impedance continuously, and was removed for reference hydration level measurement by the moisture meter (e.g., 3 sec on skin and 2 minutes and 50 seconds between different conditions). However, two different kinds of noise mode, "contact effect" and "sweat effect", were observed during the experiments, and lead to unreliable results. Still, correct curves of measurement were achieved after the influence of contact effect and sweat effect were eliminated. The results show the impedance measured by hydration sensor as function of frequency in different hydration levels from 32 to 90 by applying body lotion on skin. The impedance decreases with increasing frequency due to reduction of the imaginary part of impedance. Also, the impedance decreases with increasing hydration level since the permittivity and conductivity of skin increased.

Impedance as a function of hydration levels at different measuring frequencies from 10 kHz to 100 kHz were also determined. As frequency increases, the impedance decreases since the imaginary part (capacitance part) of the impedance decreases. Comparing the reduction of impedance magnitude between at 10 kHz and 100 kHz, there is 87% and 85%, respectively. It represents that sensitivity is higher in 10 kHz than in 100 kHz. Based on the above, trials were executed at a fixed frequency of 10 kHz showing that as hydration level increases, the impedance magnitude is reduced.

Applicant performed real-time skin hydration monitoring on the human body using sensors 225 on ESS patch 200. In order to demonstrate the hydration level variation within the volunteer subject, an "espresso scenario" was performed whereby the subject keeps calm from a starting point of measurement to 240 seconds, and then drinks a can of iced espresso. In the calm region, the hydration level slightly increases from 69 to 83 and 78 to 90, as measured by sensor 225 and by the control meter, respectively. In contrast, the hydration level is elevated significantly in the following 360 seconds (78 to 93 by sensor 225, and 90 to 103 by the control meter). This may be due to the espresso causing body sweating and elevating the hydration level. Interestingly, the hydration level drops gradually in the last 240 seconds due to the body cooling down. During the whole period of measurement, the converted results of impedance measured by sensor 225 exhibits excellent consistency corresponding to the results of the control meter.

Al-Coil-Based Wireless Strain Gauge

Deformation of the skin is captured by the wireless passive Al coil (227) surrounding the sensors and can be wirelessly transferred to a reader via electromagnetic field (see FIG. 5(*a*)). This passive Al coil can also be used as the NFC antenna for the EP, hydration and temperature sensors in some cases, which ensures the potential capability of the wireless communication of the ESS patch. The resonant frequency of an LRC circuit depends on its inductance and capacitance (see equation (1)). Miniaturized capacitors are low in cost and can be integrated into small chips and easily plugged into most circuits. However, since the ESS structure needs to be planar, flexible, and thin, adding discrete capacitors involves connecting more components which can reduce robustness, increase cost, and increase the "real estate" footprint. To solve this issue, an embodiment has the resonant frequency largely set by the inductor (as discussed above) so any change in inductance produces a large change in the frequency (which can then be translated to change in temperature and the like). Inductance mostly depends on the layout of the circuit in an embodiment (e.g., element 227 of FIG. 2(*a*)). As discussed above, a planar circuit's inductance depends on the number of turns the strand takes, the shape of the turns, and the area that is covered by the circuit.

In an embodiment, the passive wireless sensor 200 consists two layers of Al-on-PET films in which the first layer forms the majority of the serpentine structures 225, 226, 227, 228 and the second layer forms the small bridge 253 that crosses over the first layer with its PET side facing the Aluminum side of the first layer. The Al-PET-Al structure at the round pads 251, 252 form parallel plate capacitors connected in series (in one embodiment the calculated capacitance is $3.76 \times 10^{-12}$ F) and the serpentine wires act as both an inductor and a resistor, which results in a standard RLC circuit (see bottom panel of FIG. 5(*a*)). Since inductance largely depends on the number of turns of strands in sensor 227, shape of the turns, and the area that is covered by the circuit, an embodiment has been formulated that shifts the resonant frequency of the circuit by stretching or compressing or even bending sensor 227.

For example, in FIG. 5(*a*) a reader coil 528 was connected to an Impedance Analyzer via a BNC-RCA adaptor. The reader coil 528 was inductively coupled to sensor 527 (analogous to coil 227), which acts as the secondary coil in this transformer like setup (i.e., two coils separated from each other by a distance). The resonant frequency of the sensor 527 was obtained by measuring the impedance response of the coupled circuit as a function of frequency. The resonant frequency corresponds to a dip in the phase-frequency curve of the impedance response. The trial setup is shown in FIG. 5(*b*).

Before making any measurement on the wireless sensor 527, Applicant measured the resonant frequency of the reader 528. Then Applicant performed a stretching test of the coil (FIG. 5(*c*) and middle panel of FIG. 5(*a*)) and resonant frequency of the reader at each applied strain was recorded (FIG. 5(*d*)). FIG. 5(*d*) shows the resonant frequency of the coil shifts from 38.6 MPa at 0% strain to 34.2 MPa at 27% strain. Notably, the ability of reading resonant frequency at 27.0% strain itself validates that the sensor stays integrated up to 27% strain. Resonant frequency as a function of applied strain is plotted as line 529 in FIG. 5(*e*), which shows there is a monotonic negative relationship between resonant frequency and applied strain. Details of the resonant frequency corresponding to each applied strain can be found in the following table:

| | Applied strain | | | | |
|---|---|---|---|---|---|
| | 0% | 6.8% | 13.5% | 20.3% | 27.0% |
| RF(MPa) | 38.6 | 36.6 | 35.4 | 34.3 | 34.2 |
| Change in FR (%) | 0 | −5.18 | −8.29 | −11.14 | −11.40 |

An explanation (proportional relation) for the negative monotonic relationship between resonant frequency and the applied strain is that stretching of the antenna 527 increases the area of the antenna, which increases the inductance and thus reduces the resonant frequency. The inductance of a coil is approximately proportional to the square root of the area that is covered by the coil $$L_0 \sim \sqrt{A} \sim \sqrt{l_1 l_2} \qquad (4)$$

where $l_1$ and $l_2$ are the dimensions of the outer-most turns of the planar coil in the longitudinal and transverse/horizontal directions.

For stretching (where ν Poisson's ratio of the material):

$$l_{1(\varepsilon)} = l_1 \times (1+\varepsilon), l_{2(\varepsilon)} = l_2 \times (1-\nu\varepsilon) \qquad (5)$$

Then:

$$L_{(\varepsilon)} \sim \sqrt{A_{(\varepsilon)}} \sim \sqrt{A(1+\varepsilon)(1-\nu\varepsilon)} \sim L_0 \sqrt{(1+\varepsilon)(1-\nu\varepsilon)} \qquad (6)$$

$$f_{(\varepsilon)} = \frac{1}{2\pi\sqrt{L_{(\varepsilon)}C}} \sim f_0 \frac{1}{[(1+\varepsilon)(1-\nu\varepsilon)]^{0.25}} \sim f_0 \left(1 + \frac{1}{4}(\nu-1)\varepsilon\right) \qquad (7)$$

where a character with a subscript "ε" denotes that characteristic when stretched and a subscript "0" denotes that characteristic before stretching. The "~" symbol in equations (6) and (7) denotes "proportional".

Planar rectangular inductor theory predicts inductance of the circuit in different applied strains. In this theory geometry of the rectangular circuit with straight lines is used to calculate the self-inductance and mutual-inductance in an iterative manner and ultimate inductance is the summation of all the self-inductance ($L_o$) and mutual-inductance (M).

$$L = \Sigma L_0 + \Sigma M \qquad (8)$$

The predicted result by using both of the theories are plotted in FIG. 5(*e*) (see lines corresponding to Equations 7 and 8). The theoretical result and experimental result exhibit excellent agreement in predicting the trend of resonant frequency as a function of the applied strain.

The effect of the distance (coupling factor k) between reader coil 528 and sensor coil 527 was tested and shows the resonant frequency of the coil 527 is almost independent of the distance between the coils whereas the phase is not. Specifically, the closer the reader is to the coil, the larger the phase is deviated from 90 degrees, which is the phase of the reader only (i.e., before one puts the reader 528 close to the reader), thus the higher Q factor.

In FIG. 5(*f*), an on skin deformation measurement was performed by placing the passive wireless coil sensor 527 on the outer side of the wrist and putting the wrist with the coil close to the reader 528. Three layers of tattoo adhesive film were applied between the coil sensor and the skin to enhance the adhesion. Applicant performed three positions of the hand, which are "flat", "stretch" and "compress", as shown in FIG. 5(f). For the "flat" position the subject held his hand so the hand and arm formed a straight line. For the "stretch" position the hand was bent downwards to an extreme position so the coil sensor 527 is fully stretched. For the "compress" stage the hand was bent upwards to an extreme position so the coil sensor is fully compressed. Results of the resonant frequency in the three positions are plotted in FIG. 5(g), which reveals several interesting phenomena. First, the resonant frequency drops from 38.6 MPa to 13.92 MPa when coil 527 is applied on the skin. This is due to the loading of the skin. The second observation is that "stretch" reduces the resonant frequency (from 13.92 MPa to 12.99 MPa, −6.69% in change) whereas "compress" slightly increases resonant frequency (from 13.92 MPa to 14.41 MPa, 3.52% in change). Different from the stretch test, resonant frequency change in the on skin test is due to the combination of the deformation of the coil 527 as well as the change of the relative position to the reader 528. The reason why the phase of resonant frequency for position "stretch" increases is because when the hand is bent away from the reader, the effective distance of the reader to the coil increases and the longer distance results in a shallower dip in the frequency sweeping curve. Repeatability tests were conducted by repeating the hand position sequence ("flat" then "stretch" then "compress") twice, which showed the initial results were repeatable.

In an embodiment the passive Al coil 527 may transfer the local signal of the ECG sensors 228 wirelessly to a remote receiver (see FIG. 7 for an example of a remote receiver) via coil 528, which is extremely useful for noncontact diagnostics. In order to transfer the data properly, an embodiment ensures the resonant frequency does not change significantly during the transferring process. Applicant placed the Al coil 527 on the chest of the subject and a resonant frequency result was obtained when the subject exhibited deep inhalation and exhalation and showed that the resonant frequency changes from 13.06 MPa to 12.80 MPa (i.e., 1.99% in change) for both of the deep inhalation and exhalation. However, the curve for inhalation is more severely sloped than that of the exhalation which is due to the fact that when the subject breathes in the chest moves towards the reader whereas when the subject breathes out the chest moves away from the reader. The insensitivity of resonant frequency to inhalation and exhalation (which can be accommodated) makes it possible for the coil to be used in an antenna application.

Figure 5C:
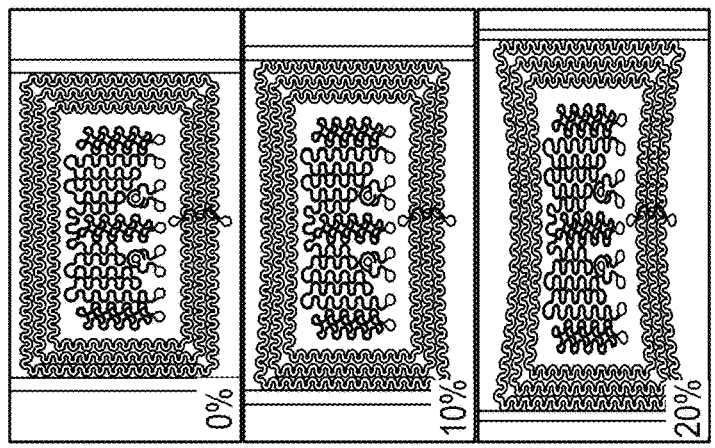
FIGS. 5(a)-(g) include images concerning a strain gauge and antenna in an embodiment of the invention.
Figure 5B:
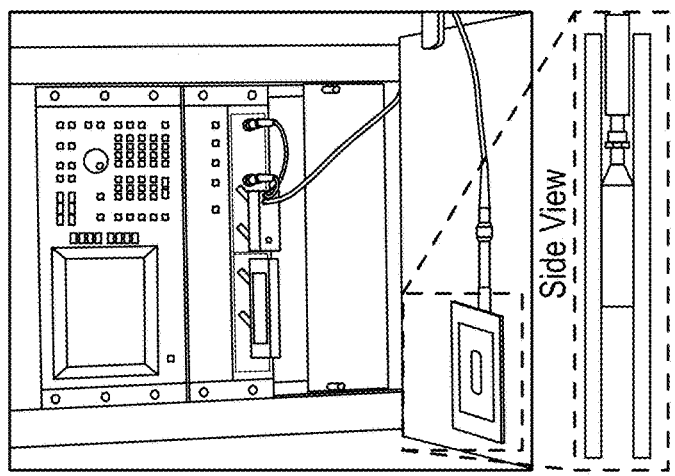
Figure 5A:
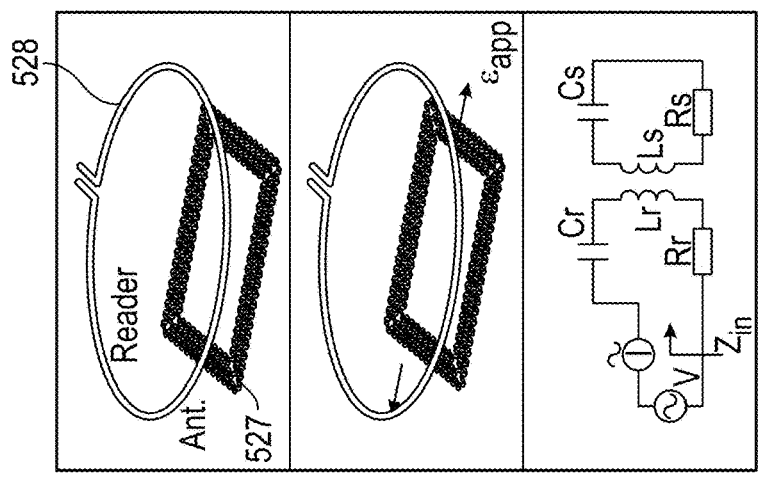
Figure 5D:
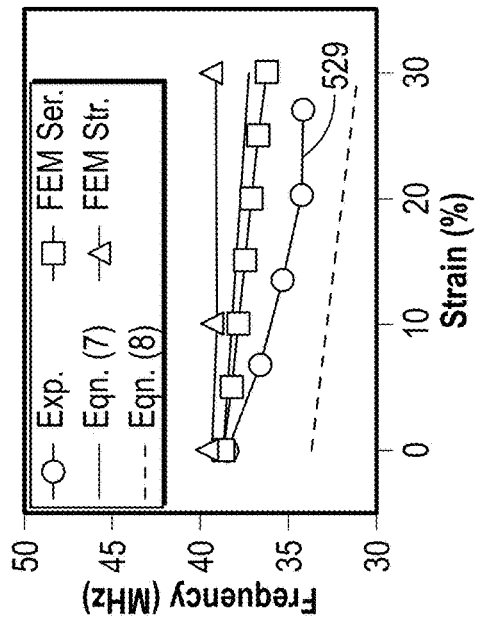
Figure 5E:
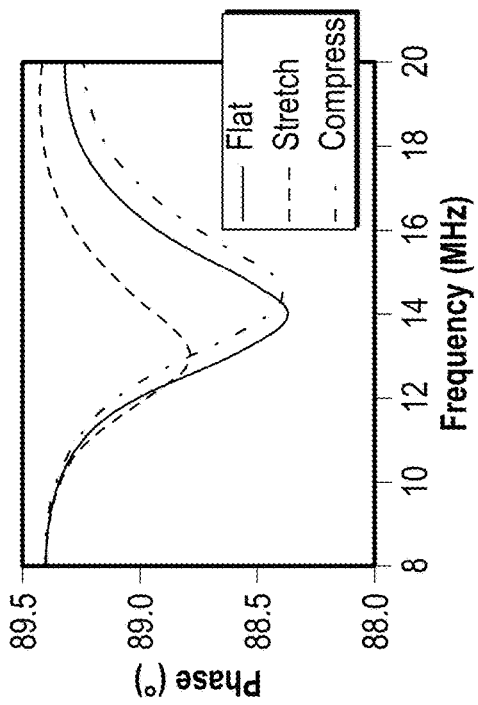
Figure 5F:
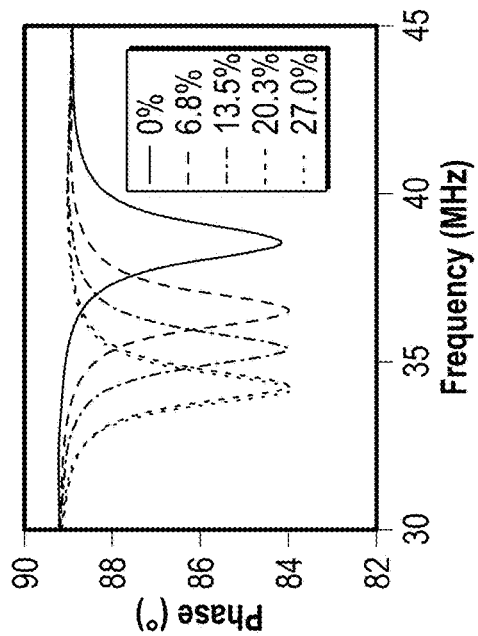
Figure 5G:
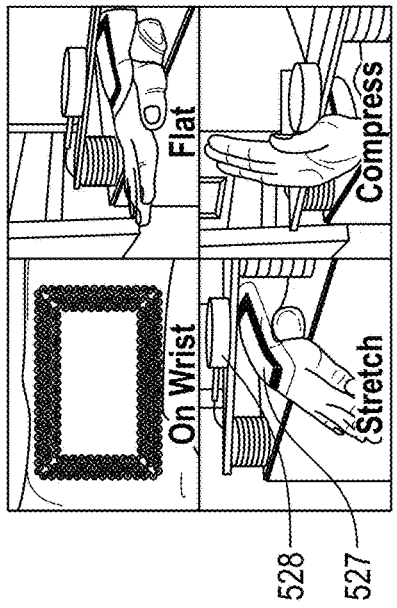

Thus, coil 527 may intentionally exhibit a shift in the resonant frequency under stretch and may be used to measure stretch in some applications (e.g., bending a limb like that shown in FIG. 5(f)). However, instead of or in addition to being used as a strain gauge, 227 can also potentially be designed as wireless antenna to transmit data. For example, in a situation where less flexing/stretching occurs functioning as an antenna may be ideal. Such a situation may occur with system 200 on the chest used to record EP signals via sensors 228 and then transmit that data via antenna/coil 227. While coupling between elements 228 and 227 is not shown in FIG. 2(a) such coupling could be performed by a person having ordinary skill in the art. The transmitted data could be processed using a system such as the system of FIG. 7.

FIG. 8 depicts a process stage in an embodiment of the invention. FIG. 8 assumes process steps from FIGS. 2(a)-(e) have occurred producing skin tape 141 coupled to strands 125, 126 but having TRT layers 103, 104 removed. FIG. 8 further assumes the process steps from FIGS. 2(a)-(e) have occurred a second time, however in this case the PET/Au 101,102 combination from FIG. 2(a) is replaced with an Al/PET element that has "flipped" in relation to the PET/Au orientation. As a result Al strands 109, 110 are now in contact with tape 141 and PET 101 is further away from tape 141. In FIG. 8 TRT layers 103', 104' (analogous to layers 103, 104 from FIG. 1(a)) are still contacting strands 191, 192. However, as was the case in FIG. 1(f), TRT layers 103', 104' will be removed and replaced with liner 142, which will then cover, directly or indirectly, each of strands 191, 192, 125, 126. Notably, in an embodiment aluminum elements 109, 110 have a height 193 greater than a height 194 for Au elements 125, 126. Further, strands 191, 192 have height 195 greater than a height 196 for strands 125, 126.

Thus, FIG. 8 addresses an alternative embodiment whereby two independent transfers (first Au patterns and then Al patterns or vice versa) occur, with the "longhorn" patterns (see FIG. 2(a)) as the alignment markers so the relative position between the Au and Al patterns can be achieved as designed. The use of different materials within a single ESS allows for a thick metal to be used for the antenna 227 (while a thin metal is used for other sensors like sensor 228). The thick metal offers lower resistance than the thin strands used for sensor 228 and the like. The lower resistance reduces antenna loss. Al is used because in the quantities needed for the thickened strand Au may be cost prohibitive.

While FIG. 8 implies "two passes" to include an Al layer and an Au layer, the process may repeat to add still additional layers and/or materials. Also, the use of the term "layer" here does not diminish the fact that in an embodiment both Au and Al both directly contact a substrate, such as skin tape 141. Note the thickness increase for the Al is gained by increasing its height 193 (versus height 194). The width 197 of the Al strands is equal to the width 198 of the Au strands in this embodiment. This promotes flexibility or stretch for the Al strands (whereas making the Al strands with a wider width 197 may lead to greater failure rates under typical stresses experienced by ESS). Furthermore, increasing width 197 would consume valuable real estate on the ESS, thereby reducing room for other sensors in a multiparametric ESS (where real estate is at a premium). In an embodiment, the heights 190, 199 for PET components of the strands may be equal or unequal to each other. In an embodiment, the widths (197, 198) for PET components of the strands may be equal or unequal to each other. Further, the "flip flopping" of the Al/PET and PET/Au helps keep the Au in direct contact with the skin (once any liner is removed and the ESS is applied to the patient) and the Al not in contact with the skin (to promote biocompatibility concerns whereby exposure of skin to Al may be undesirable).

Figure 10:
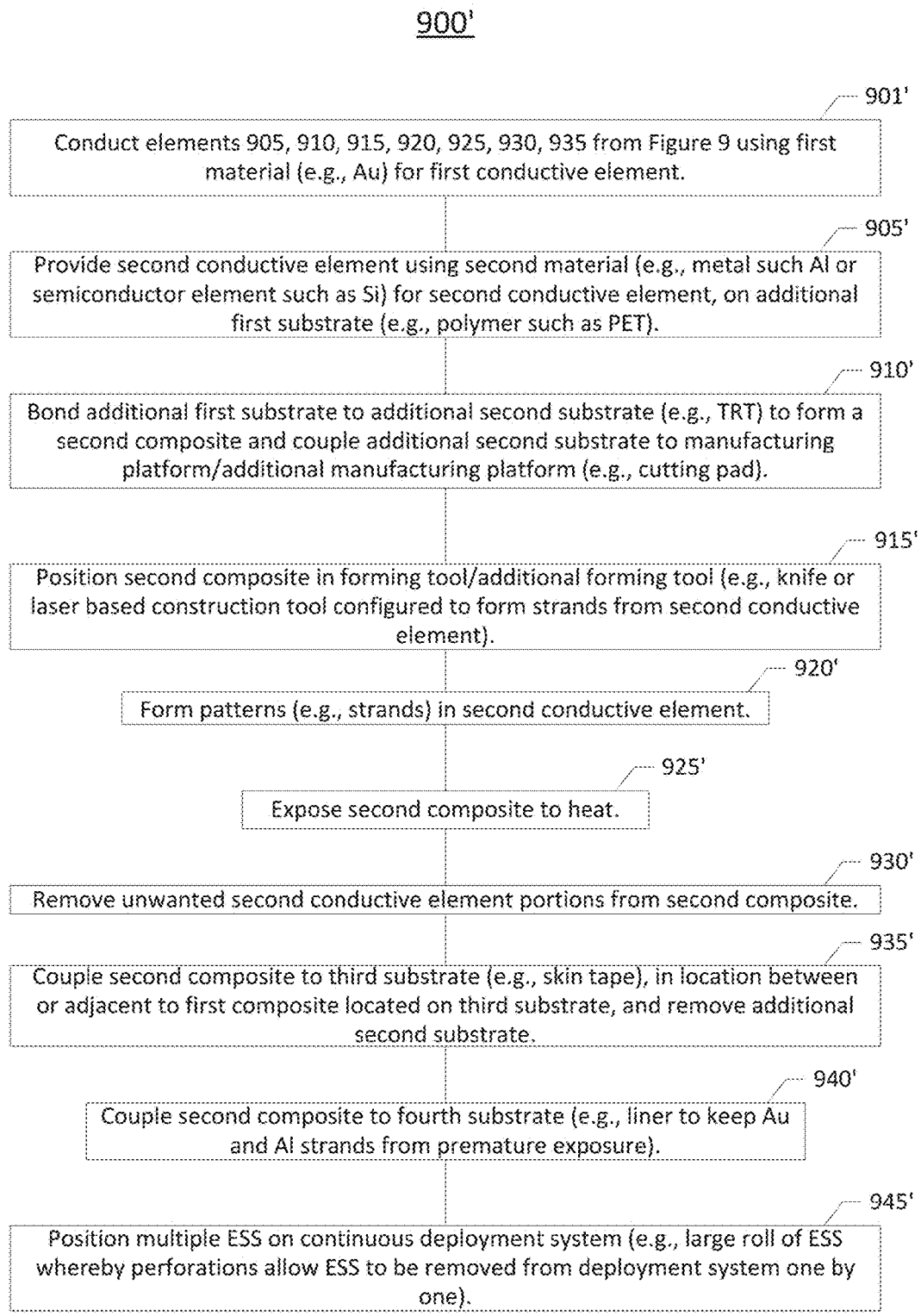
FIG. 10 includes a process for forming an ESS in an embodiment of the invention.

FIG. 10 includes process 900' with elements 901' ("Conduct elements 905, 910, 915, 920, 925, 930, 935 from FIG. 9 using first material (e.g., Au) for first conductive element"); 905' ("Provide second conductive element using second material (e.g., metal such Al or semiconductor element such as Si) for second conductive element, on additional first substrate (e.g., polymer such as PET)"); 910' ("Bond additional first substrate to additional second substrate (e.g., TRT) to form a second composite and couple additional second substrate to manufacturing platform/additional manufacturing platform (e.g., cutting pad)"); 915' ("Position second composite in forming tool/additional forming tool (e.g., knife or laser based construction tool configured to form strands from second conductive element)" which may necessarily include multiple substrates (e.g., "additional first substrate" and "additional second substrate") in the forming tool/additional forming tool); 920'

("Form patterns (e.g., strands) in second conductive element"); 925' ("Expose second composite to heat"); 930' ("Remove unwanted second conductive element portions from second composite"); 935' ("Couple second composite to third substrate (e.g., skin tape), in location between or adjacent to first composite located on third substrate, and remove additional second substrate"); 940' ("Couple second composite to fourth substrate (e.g., liner to keep Au and Al strands from premature exposure"); 945' ("Position multiple ESS on continuous deployment system (e.g., large roll of ESS whereby perforations allow ESS to be removed from deployment system one by one)").

Respiration Rate Measurement

Unlike conventional micro fabrication techniques, the cut and paste approach can be applied to a much broader category of materials. Applicant fabricated a functional stretchable strain gauge system, which includes electrically conductive rubber (ECR; Elastosil® LR 3162, Wacker Silicones) as the resistor component and 100 nm gold serpentine wire as the stretchable interconnect, by exploiting an embodiment of the cut and paste method.

Figure 6A:
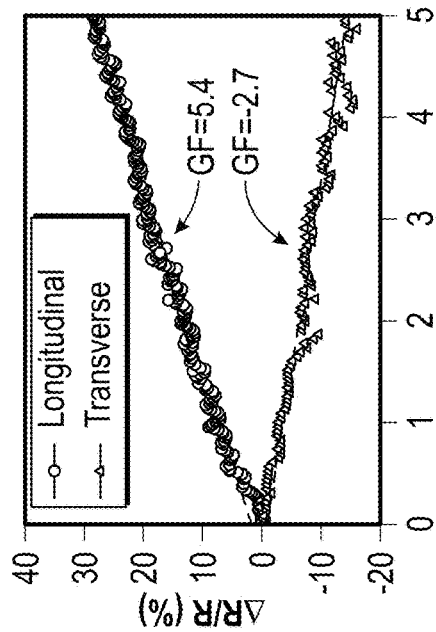
FIGS. 6(a)-(h) include images and analysis concerning a respiratory rate sensor in an embodiment of the invention.

Three types of strain gauges are fabricated as shown in FIG. 6(a). The longitudinal strain gauge 601 and transverse strain gauge 602 are used to measure the strain corresponding to longitudinal and transverse directions by measuring the change in resistance in the gauges. The Wheatstone bridge based gauge 603 is used to measure the temperature-effect-free strain by measuring the voltage in the gauge. A property of a strain gauge is its Gauge Factor (GF), which is defined as the ratio of the fractional resistance change ($\Delta R/R_0$) to the applied strain ($\varepsilon$):

$$GF = \frac{\Delta R / R_0}{\varepsilon} \quad (9)$$

Figure 6B:
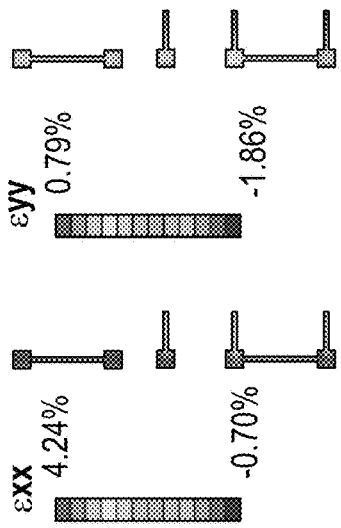

The GF of 601 and 602 are measured with tensile strain applied along the vertical direction and the results are plotted in FIG. 6(b). The GF of 601 is 5.4 and the GF of 602 is −2.7 as it is subjected to horizontal compressive strain due to Poisson's effect of the Tegaderm™ substrate.

In an embodiment design of the strain gauge system follows a basic principle of skin-mountable strain gauges where the idea is to configure the system by using different in-plane geometry and different materials so the overall resistance change of the system approaches the local resistance change of the resistors.

Figure 6C:
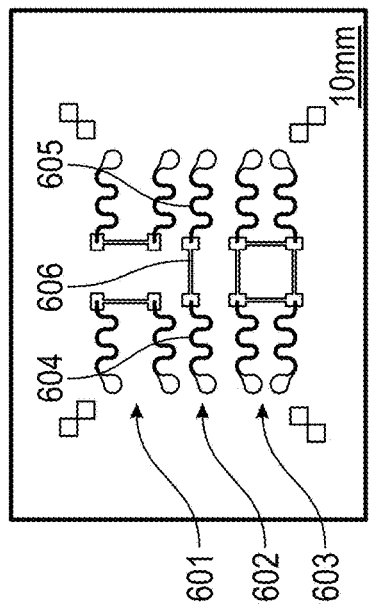
Figure 6D:
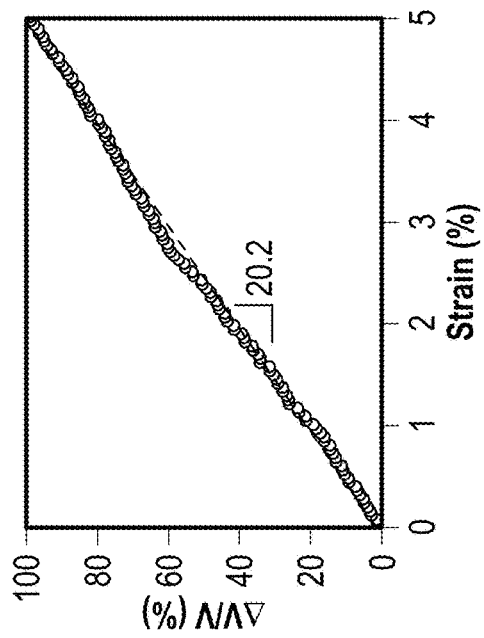

For increased accuracy, Wheatstone bridge 603 is adopted to eliminate the temperature effect. Input voltage is applied across two diagonal vertices of the bridge and output voltage is measured across the other two diagonal vertices. The result of the fractional voltage change as a function of strain is plotted in FIG. 6(c). This shows the curve is linear up to 5% strain and the slope, which is a GF-like parameter for the Wheatstone bridge equal to 20.2. FEM results are in FIG. 6(d) and show the longitudinal resistor properly accommodates the longitudinal strain and the transverse resistor takes care of the transverse strain.

Figure 6F:
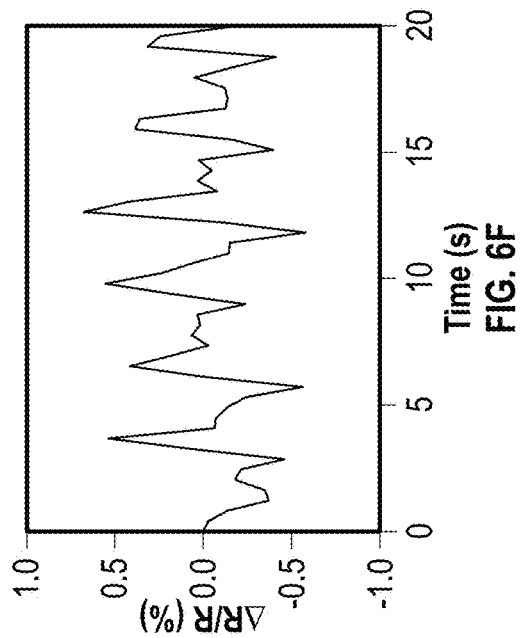
Figure 6H:
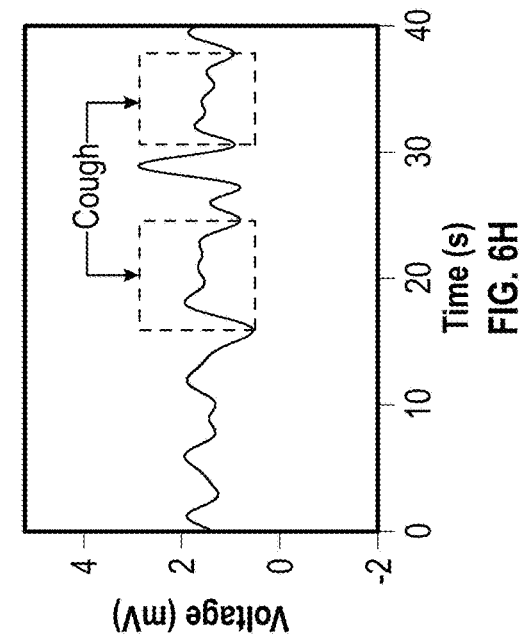
Figure 6E:
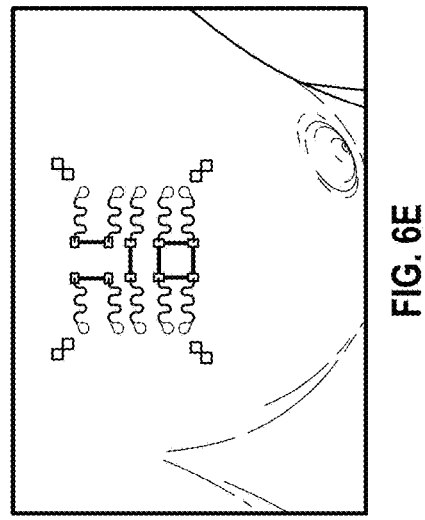
Figure 6G:
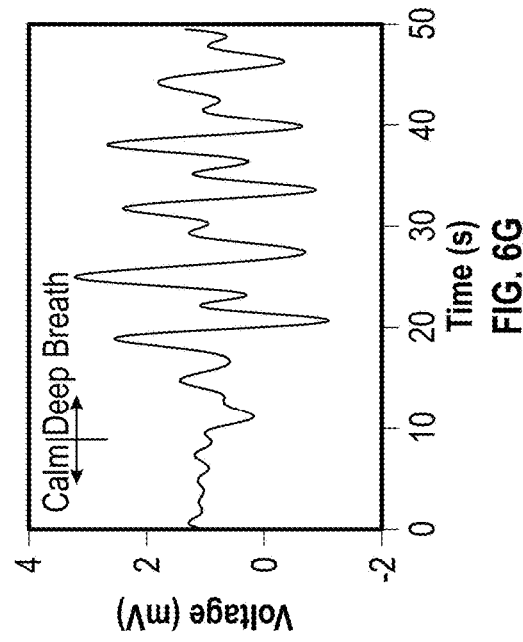

FIGS. 6(e)-(h) illustrate an on skin test performed by applying the strain gauges of FIG. 6(a) on the chest of the subject during various respirational patterns. FIG. 6(f) shows the real time measurement of the resistive result for normal respiration rate by using a longitudinal resistor 601. The respiratory rate of the male subject is measured to be 6 inhalation-exhalation cycles in 20 seconds, which exhibits good consistency with the normal statistic respiratory rate of 16 to 20 times per minute. FIGS. 6(g)-(h) respectively show three different respiration patterns measured in real-time, including quiet breathing, deep breathing, and coughing. The figures show deep breathing induces more intense voltage change than quiet breathing, which means the chest moves more for deep breathing than quiet breathing. Also, the respiratory frequency for deep breathing is smaller than that of quiet breathing. To be specific, in deep breathing the subject takes about 2 seconds for inhalation and 3 seconds for exhalation, which is much longer that than that of the quiet breathing. Respiration rate for coughing is also captured by the Wheatstone bridge, with repeated patterns due to multiple coughs shown in FIG. 6(h).

ESS discussed herein may utilize a system such as the system of FIG. 7, discussed below. For example, EP signals from sensors 228 may be wired to a node such as node 1000 (via direct wiring contacting pads 228') whereby node 1000 processes and displays the signals and performs measurements (e.g., R-R intervals). However, in other embodiments the signals may communicated via wireless means using antenna 227. Embodiments may be used in many different types of systems. For example, in one embodiment a communication device (e.g., Smartphone) can be arranged to perform the various methods and techniques described herein. Of course, the scope of the present invention is not limited to a communication device, and instead other embodiments can be directed to other types of apparatus for processing instructions.

Program instructions may be used to cause a general-purpose or special-purpose processing system that is programmed with the instructions to perform the operations described herein. These instructions may be used to process signals (e.g., EP signals) or program a machine to cut or otherwise form (e.g., via knife or laser) strands for an ESS. Alternatively, the operations may be performed by specific hardware components that contain hardwired logic for performing the operations, or by any combination of programmed computer components and custom hardware components. The methods described herein may be provided as (a) a computer program product that may include one or more machine readable media having stored thereon instructions that may be used to program a processing system or other electronic device to perform the methods or (b) at least one storage medium having instructions stored thereon for causing a system to perform the methods. The term "machine readable medium" or "storage medium" used herein shall include any medium that is capable of storing or encoding a sequence of instructions (transitory media, including signals, or non-transitory media) for execution by the machine and that cause the machine to perform any one of the methods described herein. The term "machine readable medium" or "storage medium" shall accordingly include, but not be limited to, memories such as solid-state memories, optical and magnetic disks, read-only memory (ROM), programmable ROM (PROM), erasable PROM (EPROM), electrically EPROM (EEPROM), a disk drive, a floppy disk, a compact disk ROM (CD-ROM), a digital versatile disk (DVD), flash memory, a magneto-optical disk, as well as more exotic mediums such as machine-accessible biological state preserving or signal preserving storage. The medium may be on an ESS or coupled thereto via direct or indirect means. A medium may include any mechanism for storing, transmitting, or receiving information in a form readable by a machine, and the medium may include a medium through which the program code may pass, such as antennas, optical fibers, communications interfaces, etc. Program code may be transmitted in the form of packets, serial data, parallel data, etc., and may be used in a compressed or encrypted format. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

Figure 7:
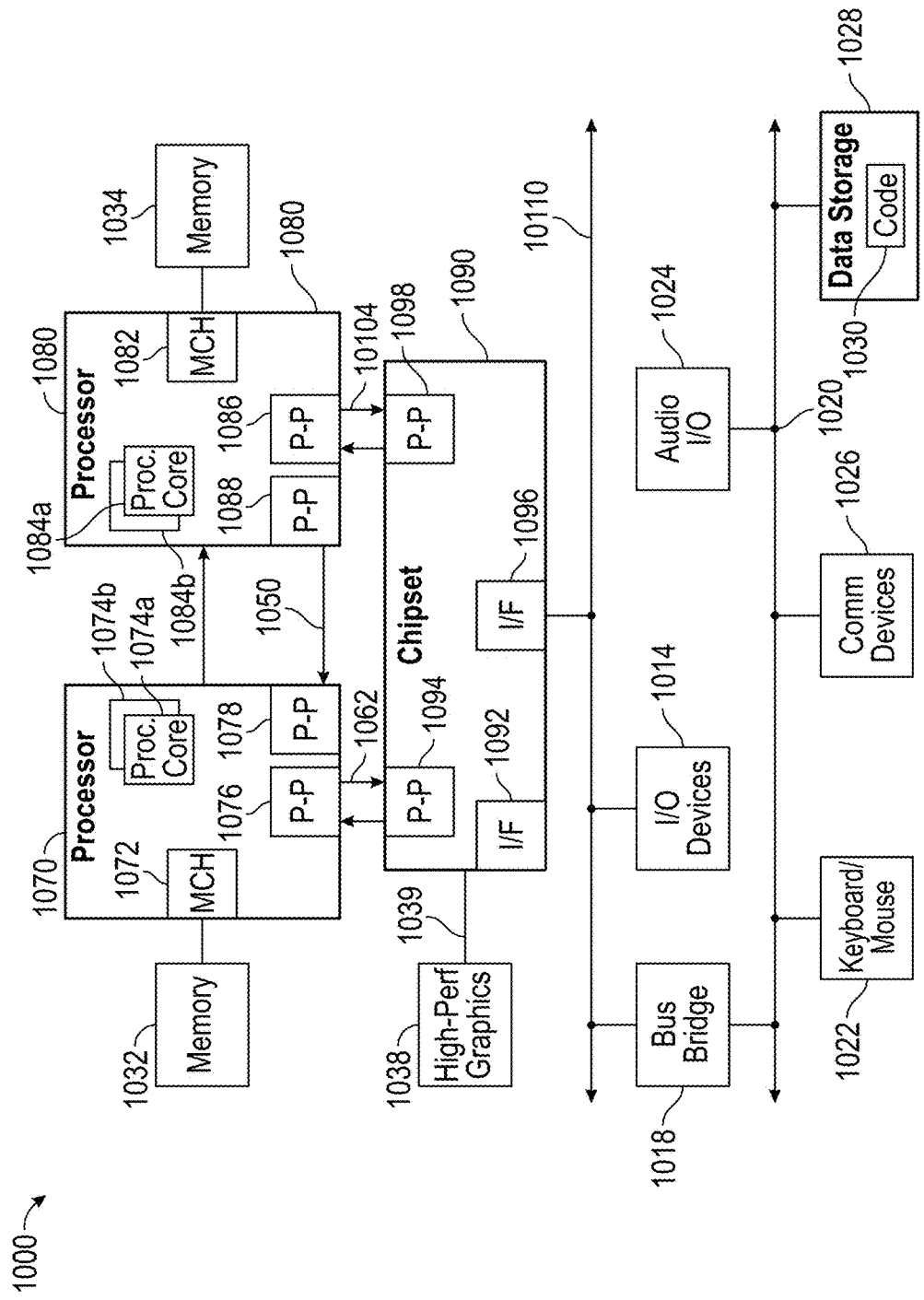
FIG. 7 includes a system for use with various embodiments of the invention.

Referring now to FIG. 7, shown is a block diagram of a system embodiment 1000 in accordance with an embodiment of the present invention. System 1000 may be included in, for example, a mobile computing node such as a cellular phone, smartphone, tablet, Ultrabook®, notebook, laptop, personal digital assistant, and mobile processor based platform.

Shown is a multiprocessor system 1000 that includes a first processing element 1070 and a second processing element 1080. While two processing elements 1070 and 1080 are shown, it is to be understood that an embodiment of system 1000 may also include only one such processing element. System 1000 is illustrated as a point-to-point interconnect system, wherein the first processing element 1070 and second processing element 1080 are coupled via a point-to-point interconnect 1050. It should be understood that any or all of the interconnects illustrated may be implemented as a multi-drop bus rather than point-to-point interconnect. As shown, each of processing elements 1070 and 1080 may be multicore processors, including first and second processor cores (i.e., processor cores 1074a and 1074b and processor cores 1084a and 1084b). Such cores 1074, 1074b, 1084a, 1084b may be configured to execute instruction code in a manner similar to methods discussed herein.

Each processing element 1070, 1080 may include at least one shared cache. The shared cache may store data (e.g., instructions) that are utilized by one or more components of the processor, such as the cores 1074a, 1074b and 1084a, 1084b, respectively. For example, the shared cache may locally cache data stored in a memory 1032, 1034 for faster access by components of the processor. In one or more embodiments, the shared cache may include one or more mid-level caches, such as level 2 (L2), level 3 (L3), level 4 (L4), or other levels of cache, a last level cache (LLC), and/or combinations thereof.

While shown with only two processing elements 1070, 1080, it is to be understood that the scope of the present invention is not so limited. In other embodiments, one or more additional processing elements may be present in a given processor. Alternatively, one or more of processing elements 1070, 1080 may be an element other than a processor, such as an accelerator or a field programmable gate array. For example, additional processing element(s) may include additional processors(s) that are the same as a first processor 1070, additional processor(s) that are heterogeneous or asymmetric to first processor 1070, accelerators (such as, e.g., graphics accelerators or digital signal processing (DSP) units), field programmable gate arrays, or any other processing element. There can be a variety of differences between the processing elements 1070, 1080 in terms of a spectrum of metrics of merit including architectural, microarchitectural, thermal, power consumption characteristics, and the like. These differences may effectively manifest themselves as asymmetry and heterogeneity amongst the processing elements 1070, 1080. For at least one embodiment, the various processing elements 1070, 1080 may reside in the same die package.

First processing element 1070 may further include memory controller logic (MC) 1072 and point-to-point (P-P) interfaces 1076 and 1078. Similarly, second processing element 1080 may include a MC 1082 and P-P interfaces 1086 and 1088. MC's 1072 and 1082 couple the processors to respective memories, namely a memory 1032 and a memory 1034, which may be portions of main memory locally attached to the respective processors. While MC logic 1072 and 1082 is illustrated as integrated into the processing elements 1070, 1080, for alternative embodiments the MC logic may be discreet logic outside the processing elements 1070, 1080 rather than integrated therein.

First processing element 1070 and second processing element 1080 may be coupled to an I/O subsystem 1090 via P-P interfaces 1076, 1086 via P-P interconnects 1062, 10104, respectively. As shown, I/O subsystem 1090 includes P-P interfaces 1094 and 1098. Furthermore, I/O subsystem 1090 includes an interface 1092 to couple I/O subsystem 1090 with a high performance graphics engine 1038. In one embodiment, a bus may be used to couple graphics engine 1038 to I/O subsystem 1090. Alternately, a point-to-point interconnect 1039 may couple these components.

In turn, I/O subsystem 1090 may be coupled to a first bus 10110 via an interface 1096. In one embodiment, first bus 10110 may be a Peripheral Component Interconnect (PCI) bus, or a bus such as a PCI Express bus or another third generation I/O interconnect bus, although the scope of the present invention is not so limited.

As shown, various I/O devices 1014, 1024 may be coupled to first bus 10110, along with a bus bridge 1018 which may couple first bus 10110 to a second bus 1020. In one embodiment, second bus 1020 may be a low pin count (LPC) bus. Various devices may be coupled to second bus 1020 including, for example, a keyboard/mouse 1022, communication device(s) 1026 (which may in turn be in communication with a computer network), and a data storage unit 1028 such as a disk drive or other mass storage device which may include code 1030, in one embodiment. The code 1030 may include instructions for performing embodiments of one or more of the methods described above. Further, an audio I/O 1024 may be coupled to second bus 1020.

Note that other embodiments are contemplated. For example, instead of the point-to-point architecture shown, a system may implement a multi-drop bus or another such communication topology. Also, the elements of FIG. 7 may alternatively be partitioned using more or fewer integrated chips than shown in the FIG. 7.

The following examples pertain to further embodiments.

Example 1 includes a sensor system comprising: a first epidermal sensor system (ESS) comprising: a first substrate; a first strand including a first polymer directly contacting the first substrate and a first metal directly contacting the first polymer; an additional first strand including an additional first polymer directly contacting the first substrate and an additional first metal directly contacting the additional first polymer; and a first protective substrate on the first metal and the additional first metal.

For example, the substrate may include skin tape or tattoo paper.

In example 2 the subject matter of Example 1 can optionally include, wherein the first strand includes a first portion and the additional first stand includes an additional first portion that is parallel to the first portion.

For example, portions 261, 262 have areas where both are moving towards the center of ESS 200 and are parallel to each other.

In example 3 the subject matter of the Examples 1-2 can optionally include wherein the first strand directly contacts the additional first strand.

For example, at location 289, strand pair 265, 266 has a transition from strand 265 to strand 266 where the two strands directly contact each other.

In example 4 the subject matter of Examples 1-3 can optionally include a second ESS comprising: a second substrate; a second strand including a second polymer directly contacting the second substrate and a second metal directly contacting the second polymer; an additional second strand including an additional second polymer directly contacting the second substrate and an additional second metal directly contacting the additional second polymer; and a second protective substrate on the second metal and the additional second metal; wherein the first and second ESSs are adjacent one another on a roll of three or more ESSs that progressively encircle a middle portion of the roll.

Thus, an embodiment allows for a roll of ESSs that can be unrolled one ESS at the time. Other systems may deploy a strip of ESSs including four or five ESSs on the single strip all co-linear with each other. Some embodiments may include a rectangular sheet having three rows of ESSs with each row including three to four ESSs.

In example 5 the subject matter of the Examples 1-4 can optionally include wherein the first and second substrates each include skin tape portions that are monolithic with each other, the first and second polymers each include polyethylene terephthalate (PET), the first and second metals each include gold, and the first and second protective substrates each include a liner.

However, in other embodiments the first and second substrates each include tattoo paper portions that are monolithic with each other.

Thus, an embodiment may provide a continuous strip of tape that extends along a roll of ESSs, whereby the tape has perforations or other areas that lack structural integrity such that a user can simply remove one ESS from another ESS. An embodiment may provide a continuous monolithic liner that extends along a roll of ESSs, whereby the liner has perforations or other areas that lack structural integrity such that a user can simply remove one ESS from another ESS. An embodiment may include continuous skin tape and liner that extend across multiple ESSs, such as a roll or sheet of ESSs.

In example 6 the subject matter of the Examples 1-5 can optionally include wherein the first and second protective substrates are monolithic with one another and include a perforated seam between the first and second protective substrates.

In example 7 the subject matter of the Examples 1-6 can optionally include wherein the first ESS comprises: a third strand including a third metal, directly contacting the first substrate, and a third polymer; and an additional third strand including an additional third metal, directly contacting the first substrate, and an additional third polymer; wherein the first protective substrate is on the third metal and the additional third metal; wherein the first metal includes a first material different from a third material included in the third metal.

In an embodiment, the first and second metals include Au and the third metal includes Al. Of course, other conductive materials may be used including Cu, Si, SiGe, and the like.

In example 8 the subject matter of the Examples 1-7 can optionally include wherein the first ESS comprises: a second strand including a second metal, directly contacting the first substrate, and a second polymer; and an additional second strand including an additional second metal, directly contacting the first substrate, and an additional second polymer; wherein the first protective substrate is on the second metal and the additional second metal; wherein the first metal includes a first material different from a second material included in the second metal.

In example 9 the subject matter of the Examples 1-8 can optionally include wherein (a) the first substrate includes a long axis in a horizontal plane, (b) the first metal includes a first height orthogonal to the horizontal plane, (c) the second metal includes a second height orthogonal to the horizontal plane, and (d) the second height is greater than the first height.

In example 10 the subject matter of the Examples 1-9 can optionally include wherein (a) the first metal includes a first width parallel to the horizontal plane, (b) the second metal includes a second width parallel to the horizontal plane, and (d) the second width equals the first width.

In example 11 the subject matter of the Examples 1-10 can optionally include wherein the first material includes gold and the second material includes aluminum.

In example 12 the subject matter of the Examples 1-11 can optionally include wherein the second strand and the additional second strand are formed in complementary serpentine patterns; wherein the second strand includes a maximum radius of curvature directly adjacent where the additional second strand includes a minimum radius of curvature; wherein the second strand includes a minimum radius of curvature directly adjacent where the additional second strand includes a maximum radius of curvature.

For example, in FIG. 3 a minimum radius of curvature 389 aligns with a maximum radius of curvature 399 for complementary serpentine pattern 390.

In example 13 the subject matter of the Examples 1-12 can optionally include wherein the second material includes aluminum and the second strand and the additional second strand are each included in a strain gauge and an antenna.

In example 14 the subject matter of the Examples 1-13 can optionally include including a second coil configured to communicate with the antenna via inductive coupling.

For example, coil 528 may be included in a kit with several ESS.

In example 15 the subject matter of the Examples 1-14 can optionally include wherein the first protective substrate directly contacts the first metal and the additional first metal.

In example 16 the subject matter of the Examples 1-15 can optionally include wherein the first strand intersects the additional first stand at a first intersection; wherein the first strand includes a minimum diameter at the intersection and widens as the first strand moves away from the intersection.

For example, FIGS. 4(*a*)-(*l*) show images of various embodiments. FIGS. 4(*a*), (*b*), and (*c*), show a new, used, and damaged blade, respectively. Cutting results with different combinations of selected cutting parameters in the Cameo® cutting machine software (where KT stands for Kapton thickness, Sh for sharpness, Ra for cutting rate, Th for thickness, NB for new blade, UB for used blade) are given as follows: FIG. 4(*d*) KT=25.4 µm, Sh=5, Ra=1, Th=7, NB, FIG. 4(*e*) KT=25.4 µm, Sh=10, Ra=1, Th=7, NB, FIG. 4(*f*) KT=25.4 µm, Sh=5, Ra=10, Th=7, NB, FIG. 4(*g*) KT=25.4 µm, Sh=5, Ra=1, Th=20 NB, FIG. 4(*h*) KT=12.7 µm, Sh=5, Ra=1, Th=7, NB, FIG. 4(*i*) KT=25.4 µm, Sh=10, Ra=1, Th=7, UB. A minimum diameter is shown at 372, 371 where clearly the portions then broaden at 362, 361. Portions 372, 373, 371 indicate areas where a knife blade stopped and pivoted or otherwise shifted causing an overcut not present in lithography based epidermal sensors. FIGS. 4(j)(k)(l) show different intersections.

Example 17 includes a method comprising: providing a first conductive element on a first substrate; coupling the first conductive element to a second substrate to form a composite; coupling the second substrate to a manufacturing platform; positioning the composite in a forming tool includes a member selected from the group comprising a knife and a laser; forming patterns in the first conductive element; exposing the composite to heat; removing unwanted first conductive element portions from the composite; and coupling the composite to a third substrate and remove the second substrate.

In an embodiment a manufacturing platform may include a table, cutting pad, glass plane, ceramic plane, and the like. In an embodiment a conductive element may include a metal (Al, Cu, Au), a conductive pure polymer or polymer composite, and the like.

In example 18 the subject matter of example 17 can optionally include comprising positioning a first epidermal sensor system (ESS) including the first conductive element adjacent a second ESS on a roll of three or more ESSs that progressively encircle a middle portion of the roll.

Example 19 includes a sensor system comprising: a first epidermal sensor system (ESS) comprising: a first substrate; a first strand including a first polymer coupled to the first substrate and a first metal coupled to the first polymer; an additional first strand including an additional first polymer coupled to the first substrate and an additional first metal coupled to the additional first polymer; and a first protective substrate on the first metal and the additional first metal.

Thus, in embodiment the first polymer need not directly contact the first substrate but may instead do so indirectly.

In example 20 the subject matter of Example 19 can optionally include wherein the first ESS comprises: a second strand including a second metal, coupled to the first substrate, and a second polymer; and an additional second strand including an additional second metal, coupled to the first substrate, and an additional second polymer; wherein the first protective substrate is on the second metal and the additional second metal; wherein the first metal includes a first material different from a second material included in the second metal.

Example 21 includes a sensor system comprising: a first epidermal sensor system (ESS) comprising: a first substrate; a first strand including a first polymer coupled to the first substrate and a first conductive element coupled to the first polymer; an additional first strand including an additional first polymer coupled to the first substrate and an additional first conductive element coupled to the additional first polymer; and a first protective substrate on the first conductive element and the additional first conductive element.

In example 22 the subject matter of Example 21 can optionally include wherein the first ESS comprises: a second strand including a second conductive element, coupled to the first substrate, and a second polymer; and an additional second strand including an additional second conductive element, coupled to the first substrate, and an additional second polymer; wherein the first protective substrate is on the second conductive element and the additional second conductive element; wherein the first conductive element includes a first material different from a second material included in the second conductive element.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side (or active surface) of a substrate or integrated circuit is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A method comprising:
   providing a first conductive element on a first substrate;
   coupling the first conductive element to a second substrate to form a composite;
   positioning the composite in a forming tool;
   performing a cut and paste process using the forming tool to cut through the composite and form patterns in the first conductive element and form patterns in the first substrate; and
   removing portions of the composite that do not form the patterns of the first conductive element and the first substrate pattern and using a vacuum gradient cup attached to each portion of the composite that does not form the patterns.

2. The method of claim 1 further comprising positioning a first epidermal sensor system (ESS) including the first conductive element adjacent a second ESS on a roll of three or more ESSs that progressively encircle a middle portion of the roll.

3. The method of claim 1, wherein performing the cut and paste process further comprises using the forming tool to form patterns in the first conductive element, exposing the composite to heat, removing unwanted portions of the first conductive element from the composite and coupling the composite to a third substrate and removing the second substrate.

4. The method of claim 1 further comprising coupling the second substrate to a manufacturing platform.

5. The method of claim 1, wherein positioning the composite in a forming tool further comprises using one of a knife and a laser to form patterns in the first conductive element.

6. The method of claim 5 further comprising exposing the composite to heat and removing unwanted first conductive element portions from the composite; and coupling the composite to a third substrate and remove the second substrate.

7. The method of claim 1, wherein performing the cut and paste process further comprising forming patterns in the first substrate.

8. The method of claim 7 further comprising removing portions of the composite that do not form the patterns of the first conductive element and the first substrate pattern.

9. The method of claim 7 further comprising placing the first conductive element pattern and first substrate pattern onto a target substrate with native adhesives.

10. The method of claim 9, wherein placing the first conductive element pattern and first substrate pattern onto a target substrate with native adhesives further comprises placing the first conductive element pattern and first substrate pattern onto one of a skin tape, a tattoo adhesive, a medical tape transparent dressing and silicone tape.

11. The method of claim 1, wherein removing the portions of the composite that do not form the patterns further comprises exposing composite to heat to deactivate adhesive and allow removal of the portions of the composite that do not form the patterns.

12. The method of claim 1 further comprising using one or more rollers to feed the first conductive element, the first substrate and the second substrate.

13. The method of claim 1, wherein providing the first conductive element formed on top of the first substrate further comprises plating the first conductive element onto the first substrate.

* * * * *